United States Patent
Mancebo

(10) Patent No.: US 11,976,321 B2
(45) Date of Patent: *May 7, 2024

(54) REAGENTS AND METHODS FOR ISOTHERMAL CHAIN REACTION

(71) Applicant: Ricardo Mancebo, Fremont, CA (US)

(72) Inventor: Ricardo Mancebo, Fremont, CA (US)

(73) Assignee: Ricardo Mancebo, Fremont, CA (US)

( * ) Notice: Subject to any disclaimer, the term of this patent is extended or adjusted under 35 U.S.C. 154(b) by 925 days.

This patent is subject to a terminal disclaimer.

(21) Appl. No.: 17/003,709

(22) Filed: Aug. 26, 2020

(65) Prior Publication Data

US 2020/0392570 A1    Dec. 17, 2020

Related U.S. Application Data

(63) Continuation of application No. 16/841,078, filed on Apr. 6, 2020, now Pat. No. 11,371,085, which is a continuation of application No. 15/521,161, filed as application No. PCT/US2015/057015 on Oct. 22, 2015, now Pat. No. 10,612,077.

(60) Provisional application No. 62/067,733, filed on Oct. 23, 2014.

(51) Int. Cl.
*C12Q 1/6837*    (2018.01)
*C12Q 1/6827*    (2018.01)

(52) U.S. Cl.
CPC ......... *C12Q 1/6837* (2013.01); *C12Q 1/6827* (2013.01)

(58) Field of Classification Search
CPC ...... C12Q 1/68; C12Q 1/6827; C12Q 1/6837; C12Q 2525/301; C07H 21/00
See application file for complete search history.

(56) References Cited

U.S. PATENT DOCUMENTS

| | | | |
|---|---|---|---|
| 5,424,413 A | 6/1995 | Hogan et al. | |
| 5,871,921 A | 2/1999 | Landegren et al. | |
| 5,925,517 A | 7/1999 | Tyagi et al. | |
| 6,451,593 B1 | 9/2002 | Wittig et al. | |
| 6,548,254 B2 | 4/2003 | Beckman et al. | |
| 6,558,928 B1 | 5/2003 | Landegren | |
| 7,582,429 B2 | 9/2009 | Wittwer et al. | |
| 10,612,077 B2 * | 4/2020 | Mancebo ............ | C12Q 1/6837 |
| 11,371,085 B2 * | 6/2022 | Mancebo ............ | C12Q 1/6827 |
| 2002/0102592 A1 | 8/2002 | Landegren | |
| 2002/0137036 A1 | 9/2002 | Sorge et al. | |
| 2003/0065155 A1 | 4/2003 | Usman et al. | |
| 2003/0129611 A1 | 7/2003 | Bao et al. | |
| 2004/0091864 A1 | 5/2004 | French et al. | |
| 2005/0287526 A1 | 12/2005 | Landegren et al. | |
| 2007/0077588 A1 | 4/2007 | Will | |
| 2007/0231808 A1 | 10/2007 | Gouda et al. | |
| 2011/0077389 A1 * | 3/2011 | Nelson ................ | C07C 255/16 548/304.1 |
| 2012/0107794 A1 * | 5/2012 | Appella ............... | C07C 271/24 435/5 |
| 2013/0210079 A1 | 8/2013 | Stanojevic et al. | |
| 2014/0170654 A1 | 6/2014 | Landegren et al. | |
| 2015/0038336 A1 | 2/2015 | Barany et al. | |
| 2017/0009278 A1 | 1/2017 | Soderberg et al. | |
| 2020/0239945 A1 | 7/2020 | Mancebo | |
| 2020/0392570 A1 | 12/2020 | Mancebo | |

FOREIGN PATENT DOCUMENTS

| | | |
|---|---|---|
| WO | WO-2002/077256 A1 | 10/2002 |
| WO | WO-2013/102150 A1 | 7/2013 |
| WO | WO-2013/123220 A1 | 8/2013 |

OTHER PUBLICATIONS

Du et al., Hybridization-Based Unquenching of DNA Hairpins on Au Surfaces: Prototypical 'Molecular Beacon' Biosensors, J Am Chem Soc, 124: 4012-4013 (2003).
Landegren et al., "A Ligase-mediated Gene Detection Technique," Science, 241: 1077-1080 (1988).
Percivalle et al., "Oligonucleotide-templated chemical reactions pushing the boundaries of a nature-inspired process," Org Biomol Chem, 11: 16-23 (2013).
Silverman et al., "Quenched probes for highly specific detection of cellular RNAs," Trends Biotechnol, 23(5): 225-230 (2005).
Tyagi et al., "Molecular Beacons: Probes that Fluoresce upon Hybridization," Nature Biotechnol, 14: 303-308 (1996).
Abe et al., "Rapid DNA Chemical Ligation for Amplification of RNA and DNA Signal", Bioconjugate Chemistry, vol. 19, No. 1, Jan. 1, 2008.
Abe et al., "Universal linkers for 1-15 signal amplification in auto-ligating probes," Nucleic Acids Symposium Series, No. 49: pp. 37-38 (2005).
Extended European Search Report for EP Application No. 22186914.2 dated Nov. 3, 2022.
Abe et al., "Destabilizing Universal Linkers for Signal Amplification in Self-Ligating Probes for RNA," J Am Chem Soc, 126: 13980-13986 (2004).
Franzini et al., "Efficient Nucleic Acid Detection by Templated Reductive Quencher Release," J Am Chem Soc, 131(44): 16021-16023 (2009).

(Continued)

*Primary Examiner* — Ethan C Whisenant
(74) *Attorney, Agent, or Firm* — Foley Hoag LLP; David P. Halstead; Mohanad Mossalam

(57) ABSTRACT

In certain aspects, the invention disclosed herein relates to the isothermal amplification of probe linkage products to generate specific amplified signals. In some aspects, the invention provides methods, reagents, and kits for carrying out such amplification via the isothermal chain reaction (ICR).

11 Claims, 8 Drawing Sheets

(56) References Cited

OTHER PUBLICATIONS

International Search Report and Written Opinion for International Application No. PCT/US2015/057015 dated Jan. 25, 2016.
Silverman et al., "Quenched Autoligation Probes Allow Discrimination of Live Bacterial Species by Single Nucleotide Differences in rRNA," Nucleic Acids Res, 33(15): 4978-4986 (2005).

* cited by examiner

REAGENTS AND METHODS FOR ISOTHERMAL CHAIN REACTION

RELATED APPLICATIONS

This application is a continuation of U.S. application Ser. No. 16/841,078, filed Apr. 6, 2020, which is a continuation of U.S. application Ser. No. 15/521,161, filed Apr. 21, 2017, now U.S. Pat. No. 10,612,077, issued Apr. 7, 2020, which claims the benefit of priority to PCT of Application No. PCT/US15/57015, filed Oct. 22, 2015, which claims the benefit of priority to Provisional Application No. 62/067,733, filed Oct. 23, 2014, which are hereby incorporated by reference in their entirety.

BACKGROUND OF THE INVENTION

Recent advances in nucleic acid testing (NAT) technologies have been aimed at isothermal methods to enable point-of-care testing (POCT) of infectious and genetic diseases. These NATs have led to improvements in enzyme-based nucleic acid amplification strategies, which have been used to detect DNAs and RNAs in prokaryotic and mammalian cells without thermocycling. Although these strategies offer the potential to develop new bioanalytical assays for SNP (single nucleotide polymorphism) detection without thermocycling, these methods typically require enzymes, multiple primers, nucleotides, and extension reactions, which limit the utility for POCT where minimal sample preparation, low cost, and rare mutation detection are key considerations. Specifically, enzyme inhibitors are found in many laboratory samples and clinical specimens, such as whole blood, urine, saliva, and CSF, which significantly increases the risk of false negatives, resulting in ambiguities around a diagnosis. Moreover, extension reactions are error-prone and could lead to inaccurate results. Additionally, co-amplification of non-target sequences without enriching the target sequence in heterogeneous samples can affect the limit of detection (LOD) for rare mutations in clinical specimens. From a cost perspective, enzymes and nucleotides significantly increase the cost of a reaction, and multiple primers add complexity and a need for repeated redesign-evaluation cycles, and hence cost to each reaction. In addition to these limitations, NATs are too slow to enable rapid POC stratification. PCR and next-generation sequencing (NGS) technologies require enzymes, nucleotides, thermocycling, extension reactions and have a LOD of only 0.1% for rare mutations, and therefore face similar challenges to those discussed above for NATs for POCT.

Accordingly, there is a need for a new technology with a low LOD and/or high sensitivity in genetically heterogeneous samples to minimize false-negative test results, enable early detection of infectious and genetic disease when therapeutic interventions are much more effective, and enable routine genetic screening in the general population, both in clinical and POC settings. Furthermore, a new technology that enables faster time-to-results would provide added benefits to treatment management, such as 1) post-operative routine monitoring of residual disease after surgical debulking for disseminated cells; 2) routine screening in doctors' offices with greatly reduced testing cycles; and 3) self-administered tests without waiting for doctor's visits.

BRIEF SUMMARY OF THE INVENTION

In certain aspects, described herein is a new non-enzymatic amplification and detection technology, called Isothermal Chain Reaction ("ICR"), that is intended to enable routine POCT, ranging from early cancer detection to pathogen identification. ICR does not require any enzymes, primers, nucleotides, master mixes, extension reactions, cDNA intermediates, or thermocycling. These benefits overcome constraints of PCR-based technologies by being resistant to enzyme inhibitors found in laboratory samples and clinical specimens, having higher specificity for rare mutations, and lowering reagent costs. ICR is anticipated to enable selective, rapid, and affordable biomarker detection of genetic and infectious diseases in non-laboratory settings without having to invest in costly instruments and labor-intensive sample preparation procedures.

In some aspects, the invention relates to amplification of probe linkage products and detection of nucleic acid template sequences at a constant temperature. More particularly, in some embodiments, the invention relates to amplification of probe linkage products and detection of nucleic acid template sequences in a continuous cycling process of hybridization and denaturation of probe nucleic acids at a constant temperature without enzymes, primers, nucleosides, extension reactions, or thermocycling. In some embodiments, the invention provides reagents and methods for amplification of probe linkage products and detection of nucleic acid templates at a constant temperature without enzymes, primers, nucleosides, extension reactions, or thermocycling.

Non-limiting examples of a "nucleic acid template" include naturally occurring, synthetically made, and artificially constructed polynucleotides derived from mononucleotides, such as DNA and RNA, which comprise nucleotide sequences. The embodiment of a nucleic acid template sequence is unaltered by modification, manipulation, replication, amplification, derivation, or source. Non-limiting examples of DNA templates include single-stranded DNA (ssDNA), double-stranded DNA (dsDNA), genomic DNA (gDNA), circular DNA, covalently closed circular DNA (cccDNA), plasmid DNA, phagemid DNA, cosmid DNA, mitochondrial DNA (mtDNA), complementary DNA (cDNA), and oligonucleotide DNA. Non-limiting examples of RNA templates include messenger RNA (mRNA), small nuclear RNA (snRNA), small nucleolar RNA (snoRNA), transfer RNA (tRNA), antisense RNA (aRNA), microRNA (miRNA), transfer-messenger RNA (tmRNA), long noncoding RNA (lncRNA), retrotransposon, viral RNA, small interfering RNA (siRNA), and ribosomal RNA (rRNA).

In certain aspects, the invention provides a method for hybridizing a probe nucleic acid to a target nucleic acid template and subsequent denaturation of the probe nucleic acid from the nucleic acid template at a constant temperature to generate a probe linkage product. According to this aspect of the invention, a "probe nucleic acid" refers to polynucleotides derived from mononucleotides, such as DNA and RNA, which contain a nucleotide sequence that hybridizes to a specific target nucleic acid template. The probe nucleic acid ("probe") has a target-complementary region ("TR") that forms a loop structure and a self-complementary region ("SR") that forms a stem conformation in the absence of target nucleic acid template. The 5' and 3' termini of the probe have a first bond-forming reactive moiety ("BFRM1") that is inactive in the stem conformation. The method according to this aspect of the invention comprises contacting the target nucleic acid template with a probe under conditions wherein the probe specifically hybridizes with the target nucleic acid template through the TR such that the SR separates and the BFRM1 undergoes a transition to an active conformation, and linkage of a nucleic acid universal linker ("UL") having a second bond-forming reactive moiety ("BFRM2") that is active at the 5' and 3' termini under conditions wherein the UL specifically joins with the 5' and 3' termini of the probe hybridized to a nucleic acid template. The probe is hybridized to the target nucleic acid template such that the active BFRM1 and the active BFRM2 are in proximity. Each active BFRM1 at the 5' and 3' termini of the probe forms a chemical bond with each active BFRM2 at the 5' and 3' termini of the UL to form a linkage product. Thus, the probe linkage product undergoes a transition to a conformation that constricts and lowers the melting temperature ($T_m$) of the TR. The constricted probe linkage product with the lower $T_m$ releases from the nucleic acid template, and a new non-constricted probe hybridizes to the unoccupied nucleic acid template sequence. The steps are repeated to amplify the linkage product. In some embodiments, the probe linkage products are isothermally disrupted from target nucleic acid template sequences, and the steps are repeated to amplify the linkage products. According to this aspect of the invention, a "probe linkage product" or "linkage product" refers to the attachment of a UL to a probe through a chemical interaction, such as a covalent bond.

In some embodiments, a first BFRM1 is at the 5' terminus of a probe and a second BFRM1 is at the 3' terminus of a probe. In some embodiments, a first BFRM1 is at the 5' terminus of a probe and a second BFRM1 is not at the 3' terminus, but instead at an internal nucleotide in the probe. In some embodiments, a first BFRM1 is not at the 5' terminus, but instead at an internal nucleotide in the probe, and a second BFRM1 is at the 3' terminus of the probe. In some embodiments, a first BFRM1 is not at the 5' terminus, but instead at an internal nucleotide in the probe, and a second BFRM1 is not at the 3' terminus, but instead at an internal nucleotide in the probe.

In some embodiments, a probe does not comprise more than 5, 6, 7, 8, 9, 10, 20, 25, 30, 35, 40, 45, 50, 55, or 60 bases. In some embodiments, a probe TR has complete complementarity to a nucleic acid template sequence. In some embodiments, a probe TR has partial complementarity to a nucleic acid template sequence.

In some embodiments, the probe TR does not comprise more than 1, 2, 3, 4, 5, or 6 bases which are not paired with the target nucleic acid template sequence. For example, the probe TR does not comprise more than 1 base which is not paired with the target nucleic acid template sequence.

In some embodiments, the probe TR comprises at least 7, 8, 9, 10, 15, 20, or 25 bases which are not paired with the target nucleic acid template sequence. For example, the probe TR comprises more than 25 bases which are not paired with the target nucleic acid template sequence.

In some embodiments, the constricted probe TR formed by linkage of the probe BFRM1 and UL BFRM2 does not comprise more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases which are not paired with the target nucleic acid template sequence. For example, the probe TR formed by linkage of the probe BFRM1 and UL BFRM2 does not comprise more than 10 bases which are not paired with the target nucleic acid template sequence.

In some embodiments, the probe SR does not comprise more than 2, 3, 4, 5, 6, 7, 8, 9, 10, 11, 12, 13, 14, 15, 16, 17, 18, 19, 20, 21, 22, 23, 24, 25, 26, 27, 27, 29, or 30 bases which are not paired with the target nucleic acid template sequence. For example, the probe SR does not comprise more than 12 bases which are not paired with the target nucleic acid template sequence.

In some embodiments, the probe SR does not comprise more than 2, 4, 6, 8, 10, or 12 bases which are self-complementary. For example, the probe SR does not comprise more than 6 bases which are self-complementary.

In some embodiments, the probe SR comprises more than 12, 14, 16, 18, 20, or more bases which are self-complementary. For example, the probe SR comprises more than 20 bases which are self-complementary.

In some embodiments, the probe SR contains a 5' single-stranded region ("ssSR") wherein the bases are unpaired and the BFRM1 is overhanging at the 5' terminus and the BFRM1 is recessed at the 3' terminus. For example, the 5' ssSR comprises more than 1, 2, 3, 4, 5, 6, 7, 8, 9, 10, 15, 20, 25, 30 bases which are unpaired.

In some embodiments, the probe SR contains a 3' ssSR wherein the bases are unpaired and the BFRM1 is overhanging at the 3' terminus and the BFRM1 is recessed at the 5' terminus. For example, the 3' ssSR comprises more than 1, 2, 3, 4, 5, 6, 7, 8, 9, 10, 15, 20, 25, 30 bases which are unpaired.

In some embodiments, the UL is a nucleic acid. In other embodiments, the UL is a non-nucleic acid chemical entity. For example, the UL is a bond-forming reactive moiety.

In some embodiments, a first BFRM2 is at the 5' terminus of a UL and a second BFRM2 is at the 3' terminus of a UL. In some embodiments, a first BFRM2 is at the 5' terminus of a UL and a second BFRM2 is not at the 3' terminus, but instead at an internal nucleotide in a UL. In some embodiments, a first BFRM2 is not at the 5' terminus, but instead at an internal nucleotide in a UL, and a second BFRM2 is at the 3' terminus of a UL. In some embodiments, a first BFRM2 is not at the 5' terminus, but instead at an internal nucleotide in a UL, and a second BFRM2 is not at the 3' terminus, but instead at an internal nucleotide in a UL.

In some embodiments, the invention provides a method for a single cycle of hybridizing a probe to a nucleic acid template and subsequent denaturation of the probe from the nucleic acid template at a constant temperature. In some embodiments, the invention provides a method for multiple cycles of hybridizing a probe to a nucleic acid template and subsequent denaturation of the probe from the nucleic acid template at a constant temperature.

In some embodiments, a cycle consisting of steps (a) and (b) is performed in less than 1, 2, 3, 4, 5, 6, 7, 8, 9 or 10 minutes. In some embodiments, the target nucleic acid template is present in the sample in a low copy number. For example, the sample comprises less than about $10^{10}$, $10^9$, $10^8$, $10^7$, $10^6$, $10^5$, $10^4$, $10^3$, $10^2$, 10, or 2 copies of target template nucleic acid sequence.

In some embodiments, the BFRM1 is an azide and the BFRM2 is an alkyne. In some embodiments, the BFRM1 is an alkyne and the BFRM2 is an azide. In some embodiments, the probe is hybridized to and denatured from a target nucleic acid template sequence at a constant temperature, comprising a single cycle that yields a probe linkage product. In other embodiments, multipleprobes are hybridized to and denatured from a target nucleic acid template sequence at a constant temperature, comprising a continuous cycle that yields multiple probe linkage products. In some embodiments, the probe is hybridized to and denatured from a target nucleic acid template sequence during thermocycling, wherein the reaction is alternately heated and cooled during a single cycle to yield a probe linkage product. In other embodiments, multiple probes are hybridized to and denatured from a target nucleic acid template sequence during thermocycling, wherein the reaction is alternately heated and cooled during multiple continuous cycles to yield a plurality of probe linkage products.

In some embodiments, the BFRM1 is an aromatic ring and the BFRM2 is an alkene. In some embodiments, the BFRM1 is an alkene and BFRM2 is an aromatic ring. In some embodiments, the probe is hybridized to and denatured from a target nucleic acid template sequence at a constant temperature, comprising a single cycle that yields a probe linkage product. In other embodiments, multipleprobes are hybridized to and denatured from a target nucleic acid template sequence at a constant temperature, comprising a continuous cycle that yields multiple probe linkage products. In some embodiments, the probe is hybridized to and denatured from a target nucleic acid template sequence during thermocycling, wherein the reaction is alternately heated and cooled during a single cycle to yield a probe linkage product. In other embodiments, multiple probes are hybridized to and denatured from a target nucleic acid template sequence during thermocycling, wherein the reaction is alternately heated and cooled during multiple continuous cycles to yield a plurality of probe linkage products.

In some embodiments, the BFRM1 is a phosphate group and the BFRM2 is a hydroxyl group in the presence of a condensing agent (for example 1-ethyl-3-(3-dimethylaminopropyl) carbodiimide (EDC). In some embodiments, the BFRM1 is a hydroxyl group and the BFRM2 is a phosphate group in the presence of a condensing agent (for example EDC). In some embodiments, the probe is hybridized to and denatured from a target nucleic acid template sequence at a constant temperature, comprising a single cycle that yields a probe linkage product. In other embodiments, multipleprobes are hybridized to and denatured from a target nucleic acid template sequence at a constant temperature, comprising a continuous cycle that yields multiple probe linkage products. In some embodiments, the probe is hybridized to and denatured from a target nucleic acid template sequence during thermocycling, wherein the reaction is alternately heated and cooled during a single cycle to yield a probe linkage product. In other embodiments, multiple probes are hybridized to and denatured from a target nucleic acid template sequence during thermocycling, wherein the reaction is alternately heated and cooled during multiple continuous cycles to yield a plurality of probe linkage products.

In some embodiments, the probe and UL comprise a dye or detectable group. In some embodiments, the probe comprises a fluorescence resonance energy transfer (FRET) donor fluorophore and/or the UL comprises a FRET acceptor fluorophore, and the probe linkage products are detected by FRET. In some embodiments, the probe comprises a FRET acceptor fluorophore and/or the UL comprises a FRET donor fluorophore, and the probe linkage products are detected by FRET. In some embodiments, the dye or detectable group is quenched by a quenching moiety in which linkage between the probe and UL separates the quenching moiety from the dye or detectable group before the probe linkage product is detected.

In some embodiments the probe nucleic acid and UL contain neither a dye nor a detectable group, and the linkage products are detected by double-stranded nucleic acid binding dyes. The method according to this aspect of the invention comprises contacting the linkage products with detector nucleic acids, wherein the detector nucleic acids and linkage products form double-stranded nucleic acid regions for nucleic acid binding dyes to intercalate and bind. According to this aspect of the invention, a "detector nucleic acid" refers to polynucleotides derived from mononucleotides, such as DNA and RNA, which contains a single-stranded nucleotide sequence that hybridizes to nucleotides in the ssSR. SR, and UL wherein the detector nucleic acid ("detector") is annealed to sequences that flank the junction sites formed by a chemical bond between an active BFRM1 and BFRM2 in a linkage product.

In certain aspects, the invention further provides reagent compositions for amplifying probe linkage products and detecting nucleic acid template sequences at a constant temperature. In some embodiments, the invention provides reagent compositions for linearly amplifying a specific probe linkage product. In some embodiments, the invention provides reagent compositions for exponentially amplifying a specific probe linkage product. In some embodiments, a reagent composition according to the invention comprises a first probe nucleic acid having a thermally stable first bond-forming reactive moiety. In some embodiments, a reagent composition according to the invention comprises a second UL having a thermally stable second bond-forming reactive moiety. In such embodiments, the first bond-forming reactive moiety forms a chemical bond with the second bond-forming reactive moiety, wherein the first probe nucleic acid and the second UL are in proximity and the first probe nucleic acid hybridizes with a target nucleic acid template sequence. In some embodiments, the first bond-forming reactive moiety is an alkyne (for example a cyclooctyne group) and the second bond-forming reactive moiety is an azide. In some embodiments, the first bond-forming reactive moiety is an azide and the second bond-forming reactive moiety is an alkyne (for example a cyclooctyne group). In some embodiments, the first bond-forming reactive moiety is an alkene (for example a trans-cyclooctene group) and the second bond-forming reactive moiety is an aromatic ring (for example a tetrazine group). In some embodiments, the first bond-forming reactive moiety is an aromatic ring (for example a tetrazine group) and the second bond-forming reactive moiety is an alkene (for example a trans-cyclooctene group). In some embodiments, the first bond-forming reactive moiety is a phosphate group and the second bond-forming reactive moiety is a hydroxyl group in the presence of a condensing agent (for example 1-ethyl-3-(3-dimethylaminopropyl) carbodiimide (EDC). In some embodiments, the first bond-forming reactive moiety is a hydroxyl group and the second bond-forming reactive moiety is a phosphate group in the presence of a condensing agent (for example EDC). In some embodiments, the first bond-forming reactive moiety is an electrophilic moiety (for example an iodo group) and the second bond-forming reactive moiety is a nucleophilic moiety (for example a thiophosphate group). In some embodiments, the first bond-forming reactive moiety is a nucleophilic moiety (for example a thiophosphate group) and the second bond-forming reactive moiety is an electrophilic moiety (for example an iodo group). The nucleophilic or electrophilic moieties may be, for example, thermally stable. In some embodiments, the probe nucleic acid and/or the UL comprises a dye or detectable group. In some embodiments, the probe nucleic acid comprises a FRET donor fluorophore and/or the UL comprises a FRET acceptor fluorophore. In some embodiments, the probe nucleic acid comprises a FRET acceptor fluorophore and/or the UL comprises a FRET donor fluorophore. In some embodiments, the dye or detectable group is quenched by a quenching moiety in which linkage between the probe and UL separates the quenching moiety from the dye or detectable group before the probe linkage product is detected. In some embodiments the probe nucleic acid and UL contain neither a dye nor a detectable group, and the linkage products are detected by double-stranded nucleic acid binding dyes. The method according to this aspect of the invention comprises contacting the linkage products with detector nucleic acids, wherein the detector nucleic acids and linkage products form double-stranded nucleic acid regions for nucleic acid binding dyes to intercalate and bind. According to this aspect of the invention, a detector nucleic acid contains a single-stranded nucleotide sequence that hybridizes to nucleotides in the ssSR, SR, and UL, wherein the detector nucleic acid is annealed to sequences that flank the junction sites formed by a chemical bond between an active BFRM1 and BFRM2 in a linkage product.

In some embodiments, the invention provides reagent compositions for amplifying a specific probe linkage product from a single target nucleic acid template sequence. In some embodiments, the invention provides reagent compositions for simultaneously amplifying multiple probe linkage products from a plurality of target nucleic acid template sequences.

In some aspects, provided herein are reaction mixtures comprising a reagent composition as described herein. In some embodiments, reaction mixtures comprise target nucleic acid template sequences, including single-stranded and double-stranded target nucleic acid template sequences. Reaction mixtures of the invention may further comprise any needed reagents, including buffers, salts, or dyes.

In certain aspects, provided herein is a kit or kits for amplifying a probe linkage product from a target nucleic acid template sequence. In some embodiments, the invention provides a kit or kits or linearly amplifying a specific probe linkage product. In some embodiments, the invention provides a kit or kits for exponentially amplifying a specific probe linkage product. The kit or kits according to this aspect of the invention comprise a first probe nucleic acid having a first bond-forming reactive moiety, and a second UL having a second bond-forming reactive moiety. In the kit or kits according to this aspect of the invention, the first probe nucleic acid and the second UL are as described for the second aspect according to the invention. In some embodiments, the kit or kits further comprise a second reagent composition as described herein, wherein the second reagent composition is designed for the amplification of at least a second probe linkage product. In some embodiments, the at least a second probe linkage product TR differs from the target nucleic acid template sequence by at least a single nucleotide or nucleotide base pair, for example 1, 2, 3, 4, 5, or 6 bases which are not paired with the target nucleic acid template sequence. For example, the probe TR does not comprise more than 1 base which is not paired with the target nucleic acid template sequence.

In some embodiments, the probe TR comprises at least 7, 8, 9, 10, 15, 20, or 25 bases which are not paired with the target nucleic acid template sequence. For example, the probe TR comprises more than 25 bases which are not paired with the target nucleic acid template sequence.

In some embodiments, the constricted probe TR formed by linkage of the probe BFRM1 and UL BFRM2 does not comprise more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases which are not paired with the target nucleic acid template sequence. For example, the probe TR formed by linkage of the probe BFRM1 and UL BFRM2 does not comprise more than 10 bases which are not paired with the target nucleic acid template sequence.

In some aspects, provided herein is a method of detecting amplification of a probe linkage product comprising: (a) contacting the target nucleic acid template sequence with a probe through the TR under conditions wherein the probe specifically hybridizes with the target nucleic acid template sequence such that the SR separates and the BFRM1 undergoes a transition to an active conformation. The probe is hybridized to the target nucleic acid template sequence such that the active BFRM1 and the active BFRM2 are in proximity and forma linkage product; (b) constricting the TR and lowering the $T_m$; (c) releasing the constricted linkage product from the target nucleic acid template sequence and repeating steps (a), (b), and (c); and (d) during steps (a), (b), or (c) detecting a change in a detectable signal, wherein the change is proportional to the amount of linkage products in the sample. For example, the signal may be a fluorescent signal. In some embodiments, step (d) comprises determining an absolute or relative amount of target nucleic acid sequence. In some embodiments, the amplification is exponential. In some embodiments, the method is used in the amplification of at least a second linkage product, for example wherein the second linkage product sequence differs from the linkage product sequence by at least a single nucleotide or nucleotide base pair, for example by 1, 2, 3, 4, 5, 6, 8, 9, 10, 15, 20, 25, or more nucleotides or nucleotide base pairs. In some embodiments, the probe linkage products are isothermally disrupted from target nucleic acid template sequences, and the steps are repeated to amplify the linkage products.

In some aspects, provided herein is a device for performing amplification of a probe linkage product, comprising: (a) an automated thermal cycler capable of maintaining a constant isothermal temperature or alternately heating and cooling at least one reaction vessel comprising the reagent composition of the invention; (b) an excitation source for optically exciting the sample and causing the sample to fluoresce; and (c) a photodetector for detecting a fluorescent signal from the sample while the amplification reaction is in progress, which fluorescent signal is proportional to the amount of amplified linkage product in the reaction vessel.

In certain aspects, provided herein is a method performing nucleic acid amplification of a first probe linkage product sequence comprising: (a) mixing, in at least one reaction vessel, a double-stranded nucleic acid binding dye with a sample comprising a reagent composition of the invention, a first detector nucleic acid, and a first target nucleic acid template sequence; (b) amplifying the first probe linkage product sequence isothermally at a constant temperature or by alternately heating and cooling the reaction vessel; (c) detecting the fluorescence of the double-stranded nucleic acid binding dye by melting first amplified linkage product sequence from detector nucleic acid in a temperature gradient to generate a first melting curve; (d) repeating the mixing, amplifying, and detecting steps with a second detector nucleic acid and a second target nucleic acid template sequence to generate a second melting curve by melting second amplified linkage product sequence in a temperature gradient, and (e) comparing the first and second melting curves to determine a difference in the nucleic acid composition of the first and second target nucleic acid sequences; (f) repeating the mixing, amplifying and detecting steps with a third target nucleic acid template sequence to generate a third melting curve; and (g) comparing the first, second, and third melting curves to determine a difference in the nucleic acid composition of the first, second, and third target nucleic acid template sequences; and so on. In some embodiments, the differences are attributable to a single nucleotide or nucleotide base pair. In some embodiments, the differences are attributable to more than one nucleotide or nucleotide base pair, for example 2, 3, 4, 5, 6, 7, 8, 9, 10, 20, 30 40, 50 or more nucleotides or nucleotide base pairs. In some embodiments, the differences are attributable to rearrangements, for example insertion of viruses and immunoglobulin rearrangements by site-specific recombination. In some embodiments, the differences are attributable to transpositions, for example transposition of transposable elements by DNA intermediates, and retroviruses by RNA intermediates. In some embodiments, the differences are attributable to splicing variants, for example alternative splice site selections to generate different exon structures. In some embodiments, the differences are attributable to insertions and deletions ("indels"), for example alterations in DNA that results in net changes of at least 1 to 50 nucleotides. According to this aspect of the invention, the differences in melting curves are attributable to a plurality of detector nucleic acids that differ by more than one nucleotide or nucleotide base pair, for example 2, 3, 4, 5, 6, 7, 8, 9, 10, 20, 30 40, 50 or more nucleotides or nucleotide base pairs.

In some aspects, the invention provides a device for performing probe linkage product amplification, comprising: (a) at least one reaction vessel comprising the reagent composition of the invention; (b) an excitation source for optically exciting the sample and causing the sample to fluoresce; (c) a photodetector for detecting temperature-dependent fluorescence levels from the sample; and (d) a processor programmed to generate a melting curve of the amplification product contained within the reaction vessel. For example, the device is configured to isothermally maintain a constant temperature or alternately heat and cool the reaction vessel.

In certain aspects, provided is a method of amplifying of a probe linkage product sequence comprising (a) contacting the target nucleic acid template sequence with a first probe through the TR and a second UL, under conditions wherein the probe specifically hybridizes with and forms a duplex with the target nucleic acid template sequence such that the SR separates and the BFRM1 undergoes a transition to an active conformation. The probeishybridizedtothetargetnucleicacidtemplatesequencesuchthattheactive BFRM1 and the UL BFRM2 are in proximity and form a linkage product, wherein the probe linkage product undergoes a transition to a conformation that constricts and lowers the $T_m$ of the TR; (b) the constricted probe linkage product with the lower $T_m$ releases from the target template nucleic acid sequence, and repeating steps (a) and (b). In some embodiments, the multiplex amplification is exponential. In some embodiments, the method is used in the multiplex amplification of at least a second probe linkage product with a second target nucleic acid template sequence, for example wherein the second target nucleic acid template sequence differs from the first target nucleic acid template sequence by at least a single nucleotide or nucleotide base pair, for example 1, 2, 3, 4, 5, 6, 7, 8, 9, 10, 20, 30 40, 50 or more nucleotides or nucleotide base pairs. In some embodiments, a cycle consisting of steps (a) and (b) is performed in less than 1, 2, 3, 4, 5, 6, 7, 8, 9, or 10 minutes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
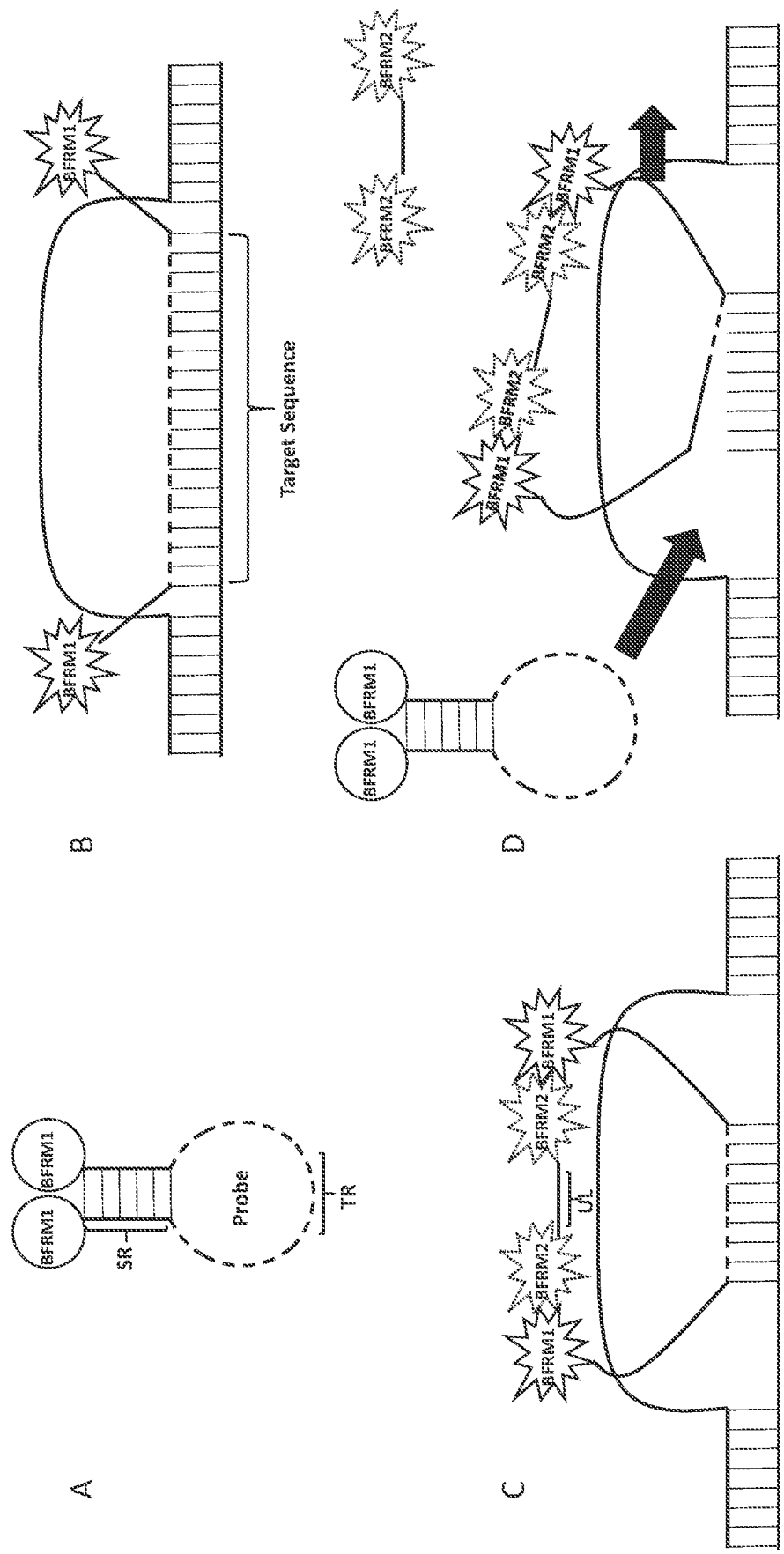
FIG. 1 illustrates an exemplary strategy and expected results from Isothermal Chain Reaction ("ICR"), in which bond-forming reactive moieties (BFRMs) join the 5' and 3' termini of a probe nucleic acid (probe) hybridized to a nucleic acid template and lower the probe $T_m$ to enable the amplification of autoligated probe linkage products at a constant temperature through a continuous isothermal progression of hybridization and denaturation of the probe from a target nucleic acid template sequence, such as a DNA biomarker. Various BFRMs can be used with ICR.

In certain aspects, the invention relates to amplification of probe linkage products and detection of nucleic acid template sequences at a constant temperature. More particularly, in some embodiments, the invention relates to amplification of probe linkage products and detection of nucleic acid template sequences in a continuous cycling process of hybridization and denaturation of probes at a constant temperature without enzymes, primers, nucleosides, extension reactions, or thermocycling. In some embodiments, the invention provides reagents, methods, kits, and devices for amplification of probe linkage products and detection of nucleic acid templates at a constant temperature without enzymes, primers, nucleosides, extension reactions, and/or thermocycling.

In certain aspects, the invention provides a method for hybridizing a probe to a target nucleic acid template and subsequent denaturation of the probe from the nucleic acid template at a constant temperature to generate a probe linkage product. In some embodiments, the invention provides a method for a single cycle of hybridizing a probe to a specific target nucleic acid template sequence and subsequent denaturation of the probe from the target nucleic acid template at a constant temperature. In some embodiments, the invention provides a method for multiple cycles of hybridizing probes to a specific target nucleic acid template and subsequent denaturation of the probes from the nucleic acid template at a constant temperature. The method according to this aspect of the invention comprises contacting the target nucleic acid template sequence with a probe under conditions wherein the probe specifically hybridizes with the target nucleic acid template, and linkage of a UL under conditions wherein the UL specifically joins with the 5' and 3' termini of the probe hybridized to the nucleic acid template. The probe is hybridized to the target nucleic acid template through the TR such that the SR separates and the BFRM1 undergoes a transition to an active conformation. The probe is hybridized to the target nucleic acid template such that the active BFRM1 and the active BFRM2 are in proximity. Each active BFRM1 at the 5' and 3' termini of the probe forms a chemical bond with each active BFRM2 at the 5' and 3 termini of the UL to form a linkage product. Thus, the probe linkage product undergoes a transition to a conformation that constricts and lowers the $T_m$ of the TR. The constricted probe linkage product with the lower $T_m$ releases from the nucleic acid template, and a new non-constricted probe hybridizes to the unoccupied nucleic acid template sequence. The steps are repeated to amplify the linkage product. In some embodiments, the probe linkage products are isothermally disrupted from target nucleic acid template sequences, and the steps are repeated to amplify the linkage products. In some embodiments, the probe linkage products are disrupted from target nucleic acid template sequences through repeated denaturation and hybridization cycles, and the steps are repeated to amplify the linkage products. In some embodiments, the probe linkage products are disrupted from target nucleic acid template sequences through a temperature gradient, and the steps are repeated to amplify the linkage products. Thus, the constricted autoligated ICR probe product releases from the nucleic acid template and initiates a signal amplification chain reaction, where a new probe follows and re-interrogates the native target nucleic acid template sequence, continuing the cycle of template-mediated signal amplification without any enzymes, nucleotides, primers, or extension reactions.

In some embodiments, nucleic acid template sequences can be single-stranded or double-stranded.

In some embodiments, the first bond-forming reactive moiety is an alkyne (for example a cyclooctyne group) and the second bond-forming reactive moiety is an azide. In some embodiments, the first bond-forming reactive moiety is an azide and the second bond-forming reactive moiety is an alkyne (for example a cyclooctyne group). In some embodiments, the first bond-forming reactive moiety is an alkene (for example a trans-cyclooctene group) and the second bond-forming reactive moiety is an aromatic ring (for example a tetrazine group). In some embodiments, the first bond-forming reactive moiety is an aromatic ring (for example a tetrazine group) and the second bond-forming reactive moiety is an alkene (for example a trans-cyclooctene group). In some embodiments, the first bond-forming reactive moiety is an electrophilic moiety (for example an iodo group) and the second bond-forming reactive moiety is a nucleophilic moiety (for example a thiophosphate group). In some embodiments, the first bond-forming reactive moiety is a nucleophilic moiety (for example a thiophosphate group) and the second bond-forming reactive moiety is an electrophilic moiety (for example an iodo group). The nucleophilic or electrophilic moieties may be, for example, thermally stable. In some embodiments, the first bond-forming reactive moiety is a phosphate group and the second bond-forming reactive moiety is a hydroxyl group in the presence of a condensing agent (for example 1-ethyl-3-(3-dimethylaminopropyl) carbodiimide (EDC)). See, for example, Prakash, G., Rubin, E. & Kool, E. T. Improved Methods for Template-Directed Cyclization of DNA Oligonucleotides. In some embodiments, the first bond-forming reactive moiety is a hydroxyl group and the second bond-forming reactive moiety is a phosphate group in the presence of a condensing agent (for example EDC).

In some embodiments, the probe and UL comprise a dye or detectable group. In some embodiments, the probe comprises a FRET donor fluorophore and/or the UL comprises a FRET acceptor fluorophore, and the linkage products are detected by FRET. In some embodiments, the probe comprises a FRET acceptor fluorophore and/or the UL comprises a FRET donor fluorophore, and the linkage products are detected by FRET. In some embodiments, the dye or detectable group is quenched by a quenching moiety in which linkage between the probe and UL separates the quenching moiety from the dye or detectable group before the probe linkage product is detected.

In some embodiments the probe and UL contain neither a dye nor a detectable group, and the linkage products are detected by double-stranded nucleic acid binding dyes. The method according to this aspect of the invention comprises contacting the linkage products with detector nucleic acids, wherein the detector nucleic acids and linkage products form double-stranded nucleic acid regions for nucleic acid binding dyes to intercalate and bind. According to this aspect of the invention, the detector nucleic acid is hybridized to sequences that flank the junction sites formed by a chemical bond between an active BFRM1 and BFRM2 in a linkage product.

In certain aspects, the invention provides reagent compositions for amplifying probe linkage products and detecting nucleic acid template sequences at a constant temperature. In some embodiments, the invention provides reagent compositions for linearly amplifying a specific probe linkage product. In some embodiments, the invention provides reagent compositions for exponentially amplifying a specific probe linkage product. In some embodiments, a reagent composition according to the invention comprises a first probe having a thermally stable first bond-forming reactive moiety. In some embodiments, a reagent composition according to the invention comprises a second UL having a thermally stable second bond-forming reactive moiety.

In some embodiments, the first bond-forming reactive moiety forms a chemical bond with the second bond-forming reactive moiety, wherein the first probe and the second UL are in proximity and the first probe hybridizes with a target nucleic acid template sequence. In some embodiments, the first bond-forming reactive moiety is an alkyne (for example a cyclooctyne group) and the second bond-forming reactive moiety is an azide. In some embodiments, the first bond-forming reactive moiety is an azide and the second bond-forming reactive moiety is an alkyne (for example a cyclooctyne group). In some embodiments, the first bond-forming reactive moiety is an alkene (for example a trans-cyclooctene group) and the second bond-forming reactive moiety is an aromatic ring (for example a tetrazine group). In some embodiments, the first bond-forming reactive moiety is an aromatic ring (for example a tetrazine group) and the second bond-forming reactive moiety is an alkene (for example a trans-cyclooctene group). In some embodiments, the first bond-forming reactive moiety is a phosphate group and the second bond-forming reactive moiety is a hydroxyl group in the presence of a condensing agent (for example 1-ethyl-3-(3-dimethylaminopropyl) carbodiimide (EDC). In some embodiments, the first bond-forming reactive moiety is a hydroxyl group and the second bond-forming reactive moiety is a phosphate group in the presence of a condensing agent (for example EDC). In some embodiments, the first bond-forming reactive moiety is an electrophilic moiety (for example an iodo group) and the second bond-forming reactive moiety is a nucleophilic moiety (for example a thiophosphate group). In some embodiments, the first bond-forming reactive moiety is a nucleophilic moiety (for example a thiophosphate group) and the second bond-forming reactive moiety is an electrophilic moiety (for example an iodo group). The nucleophilic or electrophilic moieties may be, for example, thermally stable. In some embodiments, the probe nucleic acid and/or the UL comprises a dye or detectable group. In some embodiments, the probe nucleic acid comprises a FRET donor fluorophore and/or the UL comprises a FRET acceptor fluorophore. In some embodiments, the probe nucleic acid comprises a FRET acceptor fluorophore and/or the UL comprises a FRET donor fluorophore. In some embodiments, the dye or detectable group is quenched by a quenching moiety in which linkage between the probe and UL separates the quenching moiety from the dye or detectable group before the probe linkage product is detected. In some embodiments the probe nucleic acid and UL contain neither a dye nor a detectable group, and the linkage products are detected by double-stranded nucleic acid binding dyes. The method according to this aspect of the invention comprises contacting the linkage products with detector nucleic acids, wherein the detector nucleic acids and linkage products form double-stranded nucleic acid regions for nucleic acid binding dyes to intercalate and bind. According to this aspect of the invention, a detector nucleic acid contains a single-stranded nucleotide sequence that hybridizes to nucleotides in the ssSR, SR and UL, wherein the detector nucleic acid is annealed to sequences that flank the junction sites formed by a chemical bond between an active BFRM1 and BFRM2 in a linkage product.

In some embodiments, the invention provides reagent compositions for amplifying a specific probe linkage product from a single target nucleic acid template sequence. In some embodiments, the invention provides reagent compositions for simultaneously amplifying multiple probe linkage products from a plurality of target nucleic acid template sequences.

In certain aspects, provided herein are reaction mixtures comprising a reagent composition as described herein. In some embodiments, reaction mixtures comprise target nucleic acid template sequences, including single-stranded and double-stranded target nucleic acid template sequences. Reaction mixtures of the invention may further comprise any needed reagents, including buffers, salts, or dyes.

In certain aspects, the invention provides a kit or kits for amplifying a probe linkage product from a target nucleic acid template sequence. In some embodiments, the invention provides a kit or kits or linearly amplifying a specific probe linkage product. In some embodiments, the invention provides a kit or kits for exponentially amplifying a specific probe linkage product. The kit or kits according to this aspect of the invention comprise a first probe nucleic acid having a first bond-forming reactive moiety, and a second UL having a second bond-forming reactive moiety. In the kit or kits according to this aspect of the invention, the first probe nucleic acid and the second UL are as described for the second aspect according to the invention. In some embodiments, the kit or kits further comprise a second reagent composition as described herein, wherein the second reagent composition is designed for the amplification of at least a second probe linkage product. In some embodiments, the at least a second probe linkage product TR differs from the target nucleic acid template sequence by at least a single nucleotide or nucleotide base pair, for example 1, 2, 3, 4, 5, or 6 bases which are not paired with the target nucleic acid template sequence, for example 1, 2, 3, 4, 5, 6, 7, 8, 9, 10, 20, 30 40, 50 or more nucleotides or nucleotide base pairs which are not paired with the target nucleic acid template sequence.

Non-limiting examples of reagents and methods according to the invention are shown in FIGS. 1, 2, 3, 4, and 5 which illustrate the strategy and expected results from ICR, in which the BFRM1 forms a chemical bond with the BFRM2, when the first probe and the second UL are in proximity and the first probe hybridizes with a target nucleic acid template sequence. The BFRMs join the 5' and 3' termini of a probe and lower the probe $T_m$ to enable the amplification of autoligated probe linkage products at a constant temperature through a continuous isothermal progression of hybridization and denaturation of the probe from a target nucleic acid template at a constant temperature without enzymes, primers, nucleosides, or extension reactions. In some embodiments, a first BFRM1 is at the 5' terminus of a probe and a second BFRM1 is at the 3' terminus of a probe. In some embodiments, a first BFRM1 is at the 5' terminus of a probe and a second BFRM1 is not at the 3' terminus, but instead at an internal nucleotide in the probe. In some embodiments, a first BFRM1 is not at the 5' terminus, but instead at an internal nucleotide in the probe, and a second BFRM1 is at the 3' terminus of the probe. In some embodiments, a first BFRM1 is not at the 5' terminus, but instead at an internal nucleotide in the probe, and a second BFRM1 is not at the 3' terminus, but instead at an internal nucleotide in the probe. In some embodiments, a first BFRM2 is at the 5' terminus of a UL and a second BFRM2 is at the 3' terminus of a UL. In some embodiments, a first BFRM2 is at the 5' terminus of a UL and a second BFRM2 is not at the 3' terminus, but instead at an internal nucleotide in a UL. In some embodiments, a first BFRM2 is not at the 5' terminus, but instead at an internal nucleotide in a UL, and a second BFRM2 is at the 3' terminus of a UL. In some embodiments, a first BFRM2 is not at the 5' terminus, but instead at an internal nucleotide in a UL, and a second BFRM2 is not at the 3' terminus, but instead at an internal nucleotide in a UL.

Non-limiting examples of bond-forming reactive moieties include moieties which participate in cycloaddition reactions, including azides and alkynes which participate in 'click' cycloaddition reactions. Examples of bond-forming reactive moieties for 'click' cycloaddition reactions include cyclooctyne and azide groups. See, for example, Isaac S.

Marks, Jun Sung Kang, Brady T. Jones, Kevin J. Landmark, Andrew J. Cleland, & T. Andrew Taton (2011). Strain-Promoted "Click" Chemistry for Terminal Labeling of DNA. Bioconjugate Chemistry, 22(7) 1259-1263. Other non-limiting examples of alkynes reactive with azides include octadiynyl and hexynyl groups. Octadiynyl/azide reaction occurs by a Huisgen cycloaddition "click chemistry" process that generates a covalent carbon-heteroatom bond. To increase the kinetics of the reaction, copper(I) is added as a catalyst, forming a 1,2,3-triazole between the azide and the octadiynyl alkyne. Addition of a Cu(I) catalyst has been reported to lower the activation barrier by 11 kcal mol-1 and promote regioselective autoligation. See, for example, Seela, F., Sirivolu, V. R. & Chittepu, P. (2008). Modification of DNA with Octadiynyl Side Chains: Synthesis, Base Pairing, and Formation of Fluorescent Coumarin Dye Conjugates of Four Nucleobases by the Alkyne-Azide "Click" Reaction. Bioconjugate Chem., 19(1) 211-224; and New, K. & Brechbiel, M. W. (2009). Growing Applications of "Click Chemistry" for Bioconjugation in Contemporary Biomedical Research. Cancer Biotherapy and Radiopharmaceuticals, 24(3)289-301. Hexynyl/azide reaction is similar to octadiynyl/azide, but with a hexynyl alkyne group that has a shorter linker than the octadiynyl modification.

Other non-limiting examples of bond-forming reactive moieties include moieties which participate in alkene and aromatic ring reactions. Examples of bond-forming reactive moieties for alkene and aromatic ring reactions include trans-cyclooctene and tetrazine groups that react in a tetrazine-strained inverse Diels-Alder cycloaddition reaction and has a second order rate constant $10^2$-$10^4$ times faster than the strain-promoted copper-free cyclooctyne/azide cycloaddition chemistry set. See, for example, Karver, M. R., Weissleder, R. & Hilderbrand, S. A. (2012). Bioorthogonal Reaction Pairs Enable Simultaneous, Selective, Multi-Target Imaging. Angew Chem Int Ed Engl., 51(4)920-922.

Non-limiting examples of bond-forming reactive moieties include moieties which participate in condensation reactions. Examples of bond-forming reactive moieties for condensation reactions include hydroxyl and 1-ethyl-3-(3-dimethylaminopropyl) carbodiimide (EDC)-activated phosphate utilizing a phosphate modification that reacts with a hydroxyl group to form a 3'-5' phosphodiester bond. EDC circularization of a linear oligo annealed in a Watson-Crick alignment on a complementary template has been shown to result in a 95% conversion into the ligated product at 25° C. See, for example, Prakash, G., Rubin, E. & Kool, E. T. Improved Methods for Template-Directed Cyclization of DNA Oligonucleotides.

Non-limiting examples of bond-forming reactive moieties include moieties which participate in nucleophilic/electrophilic reactions. Examples of bond-forming reactive moieties for nucleophilic/electrophilic reactions include thiophosphate and iodo groups that use a thiophosphate nucleophile to react with a custom iodo electrophilic group modification to generate an autoligation product with a phosphodiester bond that contains a sulfur atom in place of one of the bridging oxygen atoms. Iodo is a robust leaving group with a >90% conversion when attached to an oligo and paired end-to-end with a phosphorothioate-modified oligo on a template. See, for example, Xu, Y. & Kool, E. T. (1997). A Novel 5'-Iodonucleoside Allows Efficient Nonenzymatic Ligation of Single-stranded and Duplex DNAs. Tetrahedron Letters, 38(22)5595-5598. Another non-limiting example of an electrophilic group reactive with a thiophosphate nucleophile includes a dabsyl group that has previously been shown to be an efficient leaving group. See, for example, Sando, S. & Kool, E. T. (2002). Quencher as Leaving Group: Efficient Detection of DNA-Joining Reactions. J. Am. Chem. Soc., 124(10) 2096-2097. Other examples of possible bond-forming reactive moieties include thiol nucleophilic and bromoacetate electrophilic moieties, which are common generic chemistries that are commercially available. The preparation, protocol, and application of the 3'-thionucleoside thiol as a thermal-stable nucleophile are well documented in the literature. See, for example, Ghalia Sabbagh, Kevin J. Fettes, Rajendra Gosain, Ian A. O'Neil and Richard Cosstick (2004). Synthesis of phosphorothioamidites derived from 3'-thio-3'-deoxythymidine and 3'-thio-2',3'-dideoxycytidine and the automated synthesis of oligodeoxynucleotides containing a 3'-S-phosphorothiolate linkage. Nucleic Acids Research, 32(2) 495-501; Meena, Mui Sam, Kathryn Pierce, Jack W. Szostak, and Larry W. McLaughlin. (2',3'-Dideoxy-3'-Thionucleoside Triphosphates: Syntheses and Polymerase Substrate Activities. Supporting Information; Miller, G. P., Silverman, A. P. & Kool, E. (2008). New, stronger nucleophiles for nucleic acid-templated chemistry: Synthesis and application in fluorescence detection of cellular RNA. Bioorganic & medicinal chemistry, 16(1), 56-64; Meena, Mui Sam, Kathryn Pierce, Jack W. Szostak, and Larry W. McLaughlin. (2007). (2',3'-Dideoxy-3'-Thionucleoside Triphosphates: Syntheses and Polymerase Substrate Activities. Organic Letters. 9(6): 1161-1163; and Sengen Sun, Aiichiro Yoshids, and Joseph A. Piccirilli. (1997). Synthesis of 3'-thioribonucleosides and their incorporation into oligoribonucleotides via phosphoramidite chemistry. RNA 3:1352-1363.

For purposes of the invention, a "probe nucleic acid" refers to polynucleotides derived from mononucleotides, such as DNA and RNA, which contain a nucleotide sequence that hybridizes to a specific target nucleic acid template. Non-limiting lengths for probe nucleic acids and universal linker nucleic acids are from about 5 to about 80 nucleotides in length. In some embodiments, a probe does not comprise more than 5, 6, 7, 8, 9, 10, 20, 25, 30, 35, 40, 45, 50, 55, or 60 bases. The autoligation reaction occurs when a probe containing a BFRM1 at the 5' and 3' termini autoligates to a UL through the BFRM2 and places SF1 and SF2 in close proximity, resulting in a probe linkage product. Autoligation of the UL to the probe constricts the TR sequences annealed to the nucleic acid template, lowering the $T_m$ of the probe. The constricted autoligated ICR probe linkage product releases from the template and initiates a signal amplification chain reaction without thermocycling, where a new probe follows and re-interrogates the native target nucleic acid template sequence, continuing the cycle of template-mediated isothermal signal amplification without any enzymes, nucleotides, primers, or extension reactions. In some embodiments, a probe TR has complete complementarity to a nucleic acid template sequence. In some embodiments, a probe TR has partial complementarity to a nucleic acid template sequence. In some embodiments, a probe TR has complete complementarity to a nucleic acid template sequence. In some embodiments, a first BFRM1 is at the 5' terminus of a probe and a second BFRM1 is at the 3' terminus of a probe. In some embodiments, a first BFRM1 is at the 5' terminus of a probe and a second BFRM1 is not at the 3' terminus, but instead at an internal nucleotide in the probe. In some embodiments, a first BFRM1 is not at the 5' terminus, but instead at an internal nucleotide in the probe, and a second BFRM1 is at the 3' terminus of the probe. In some embodiments, a first BFRM1 is not at the 5' terminus, but instead at an internal nucleotide in the probe, and a second BFRM1 is not at the 3' terminus, but instead at an internal nucleotide in the probe. In some embodiments, a first BFRM2 is at the 5' terminus of a UL and a second BFRM2 is at the 3' terminus of a UL. In some embodiments, a first BFRM2 is at the 5' terminus of a UL and a second BFRM2 is not at the 3' terminus, but instead at an internal nucleotide in a UL. In some embodiments, a first BFRM2 is not at the 5' terminus, but instead at an internal nucleotide in a UL, and a second BFRM2 is at the 3' terminus of a UL. In some embodiments, a first BFRM2 is not at the 5' terminus, but instead at an internal nucleotide in a UL, and a second BFRM2 is not at the 3' terminus, but instead at an internal nucleotide in a UL. The term "bond-forming reactive moiety" refers to chemical functional groups that are capable of reacting with each other to form a covalent bond.

In some embodiments, disruption occurs by thermally denaturing double-stranded target nucleic acid template sequences by raising the temperature above the melting temperature.

Reaction efficiency is enhanced when the bond-forming moieties used are thermally stable. In this context, the term "thermally stable" means that the reactivity of a bond-forming moiety is not destroyed or functionally compromised to such an extent that the desired reaction no longer occurs with sufficient efficiency at temperatures required to denature the target nucleic acid template sequences.

Non-limiting examples of bond-forming reactive moieties include phosphorodithioate, phosphorotrithioate, 2',3'-cyclic phosphate, amino-deoxyribonucleoside, thiol, amine, amino, hydrazine, hydrazide, bromide, azide, thiophosphate, iodide, chloride, maleimide, dabsylate, disulfide, tosylate, alkyne, isothiocyanate, cyclooctyne, trans-cyclooctene, NHS ester, imidoester, PFP ester, alkyl azide, aryl azide, isocyanate, nitrophenyl mono- or di-ester, tetrazine, aldehyde, epoxy, 1-ethyl-3-(3-dimethylaminopropyl) carbodiimide (EDC)-activated phosphate, hydroxyl, serinol, octadiynyl, hexynyl, I-Linker, carboxylate, succinimidyl-6-hydrazino-nicotinamide, succinimidyl-4-formylbenzamide, propargyl, or boronic acid.

In some embodiments, a dye or detectable group is used to detect the ligated products formed by hybridization and autoligation. Non-limiting dyes and detectable groups include, without limitation, the groups shown in Table I below.

TABLE I

Detectable Dyes and Groups (E)-Stilbene
(Z)-Stilbene
1-Chloro-9,10-bis(phenylethynyl)anthracene
2-Chloro-9,10-bis(phenylethynyl)anthracene
2-Chloro-9,10-diphenylanthracene
5,12-Bis(phenylethynyl)naphthacene
7-AminoactinomycinD
7-Aminoactinomycin D (7-AAD)
7-Hydroxy-4-methylcoumarin
8-Anilinonaphthalene-1-sulfonate
9,10-Bis(phenylethynyl)anthracene
Acridine orange
Acridine yellow
AlexaFluor
AlexaFluor350dye, 7-amino-4-methylcoumarin
Alexa Fluor 405 dye
Alexa Fluor 430 dye
Alexa Fluor 488 dye
Alexa Fluor 514 dye
Alexa Fluor 532 dye
Alexa Fluor 546 dye
Alexa Fluor 555 dye
Alexa Fluor 568 dye TABLE I-continued Detectable Dyes and Groups Alexa Fluor 594 dye
Alexa Fluor 610 dye
Alexa Fluor 633 dye
Alexa Fluor 635 dye
Alexa Fluor 647 dye
Alexa Fluor 660 dye
Alexa Fluor 680 dye
Alexa Fluor 700 dye
Alexa Fluor 750 dye
Alexa Fluor 790 dye
Allophycocyanin
ATTO dyes
Auramine-rhodaminestain
BCECF indicator
Benzanthrone
BHQ-1
BHQ-2
BHQ-3
Bimane
Blacklight paint
blue fluorescent proteins
BOBO-1, BO-PRO-1
BODIPY 630/650 dye
BODIPY 650/665 dye
BODIPY dye
BODIPY FL dye
BODIPY TMR-X dye
BODIPY TR-X dye
Brainbow
Calcein
Calcium Crimson indicator
Calcium Green indicators
Calcium Orange indicator
Carboxy SNARF indicators
Carboxyfluorescein diacetate succinimidyl ester
Carboxyfluorescein succinimidyl ester
Cascade Blue dye
Cascade Yellow dye
Chemiluminescent
Colorimetric
Coumarin
Cy-3
Cy-5
Dabcyl
DAPI
Dark quencher
DDQ-I
DDQ-II
Di-8-ANEPPS, Di-4-ANEPPS
DiA
DID (DiIC18(5))
DiI (DiIC18(31)
DiO (DiOC18(3))
DiOC6
DiR (DiIC18(7))
DyLight Fluor
Eclipse
ELF 97 alcohol
Eosin
ER Tracker Blue-White DPX
EthD-1
Ethidium bromide
excimer/exciplex partner
exciplex dyes
FAM
Fluo-3 indicator
Fluo-4
Fluo-4 indicator
FluoProbes
Fluorescein
Fluoresceinisothiocyanate
Fluorescein, FITC
Fluoro-Jade stain
fluorophore-quenchercouples,
FM 1-43, FM 1-43FX
FM 4-64, FM 4-64FX
Fura Red indicator
Fura-2 indicator

TABLE I-continued

Detectable Dyes and Groups

Fura-2-acetoxymethylester
goldnano particles
Green fluorescent protein
HEX
Hoechst 33258, Hoechst 33342
Indian yellow
Indo-1
inorganic quantum dots
Iowa Black FQ
Iowa Black RQ
JC-1
JC-9
JOE
LC red640
LC red705
Lissamine rhodamine B
Lucifer yellow
Lucifer yellow CH
Luciferin
LysoSensor Blue DND-167
LysoSensor Green DND-153, DND-189
LysoSensor Yellow/Blue DND-160 (PDMPO)
LysoTracker Green
LysoTracker Red
Magnesium Green indicator
Marina Blue dye
Merocyanine
MGB groups
MitoTracker Green FM
MitoTracker Orange CMTMRos
MitoTracker Red CMXRos
Monobromobimane
NBD amines
NED
NeuroTrace 500/525 green-fluorescent Nissl stain
Nile blue
Nile red
Optical brightener
Oregon Green 488 dye and Oregon Green 488 BAPTA
Oregon Green 514 dye
Pacific Blue dye
Pacific Orange dye
Perylene
Phloxine
Phycobilin
Phycoerythrin
Phycoerythrobilin
POPO-1, PO-PRO-1
Propidium iodide
Pyranine
QSY-21
QSY-7
R-phycoerythrin
red fluorescent proteins
Resorufin
RH 414
Rhod-2 indicator
Rhodamine
Rhodamine 110
Rhodamine 123
Rhodamine 123
Rhodamine 6G
RhodamineGreen dye
RhodamineRed dye
RiboGreen
RoGFP
ROX
Rubrene
SERRS-active fluorescence dyes
Sodium Green indicator
Sulforhodamine101
Sulforhodamine B
SYBR Green
Synapto-pHluorin
SYTO blue-fluorescent nucleic acid stains 40, 41,
SYTO blue-fluorescent nucleic acid stains 44, 45
SYTO green-fluorescent nucleic acid stains 11, 14, 15,
SYTO green-fluorescent nucleic acid stains 12, 13, 16,
SYTO orange-fluorescent nucleic acid stains 80, 81, 82,
SYTO orange-fluorescentnucleic acid stains 84,
SYTO red-fluorescent nucleic acid stains 17, 59,
SYTO red-fluorescent nucleic acid stains 60, 62,
SYTOX Blue nucleic acid stain
SYTOX Green nucleic acid stain
SYTOX Orange nucleic acid stain
TAMRA
TET
Tetramethylrhodamine, Rhodamine B
Tetraphenyl butadiene
Tetrasodium
Texas Red
Texas Red-X dye
Titan yellow
TMR
TOTO-1, TO-PRO-1
TOTO-3, TO-PRO-3
TSO
Umbelliferone
X-rhod-1 indicator
Yellow fluorescent protein
YOYO-1, YO-PRO-1
YOYO-3, YO-PRO-3

In some embodiments, the probe and the UL are conjugated to dyes that are, respectively, a donor dye and an acceptor dye for FRET. Alternatively, the probe and UL are conjugated to dyes that are, respectively, an acceptor dye and a donor dye for FRET. In some embodiments, non-limiting examples of the donor and acceptor dyes are spaced from about 1 to about 20 nucleotides apart within the autoligation product, for example within about 1 to about 15, about 1 to about 10, about 1 to about 5, or about 1 to about 3 nucleotides. In some embodiments, the donor dye is FAM and the acceptor dye is TAMRA.

In some embodiments, the dye or detectable group is quenched by a quenching moiety in which hybridization and autoligation separates the quenching moiety from the dye or detectable group before the ligated product is detected.

In some embodiments the probe and UL contain neither a dye nor a detectable group, and the ligation products are detected by double-stranded nucleic acid binding dyes. The method according to this aspect of the invention comprises contacting the linkage products with detector nucleic acids, wherein the detector nucleic acids and linkage products form double-stranded nucleic acid regions for nucleic acid binding dyes to intercalate and bind. According to this aspect of the invention, a detector nucleic acid contains a single-stranded nucleotide sequence that hybridizes to nucleotides in the ssSR, SR, and UL, wherein the detector nucleic acid is annealed to sequences that flank the junction sites formed by a chemical bond between an active BFRM1 and BFRM2 in a linkage product.

In some embodiments, a method of the invention is used to detect the presence or absence of a mutation, for example a SNP mutation, in a biological sample. Generally, the test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acid templates. Biological samples include body fluids including but not limited to blood, urine, spinal fluid, cerebrospinal fluid, synovial fluid, amniotic fluid, semen, and saliva. Other types of biological sample may include food products and ingredients such as vegetables, dairy items, meat, meat by-products, and waste. Biological samples also include plant tissue such as seed or leaf tissue. Environmental samples are derived from environmental material including but not limited to soil, water, sewage, cosmetic, agricultural and industrial samples.

In some embodiments, a method of the invention is used to perform high resolution melt curve analysis (HRM). Nucleic acid melt curve analysis can reveal the identity of a mutation, the melting temperature, the number of nucleic acid species or purity of an amplification reaction, and thus is often used for mutation detection and as a more convenient alternative to gel electrophoresis to confirm the specificity of ICR. According to one embodiment, the nucleic acid detection is associated with HRM. Compared to regular nucleic acid melt curve analysis, HRM can yield more information on the amplified nucleic acid product, including the capability for point mutation detection (SNP), zygosity testing and epigenetics analysis. Like regular nucleic acid melt curve analysis, HRM is a post-ICR product analysis method. In HRM, a probe linkage product is first amplified by ICR in the presence of a nucleic acid binding dye and then the ICR product-dye complex is slowly melted as the fluorescence change is monitored to generate a standard nucleic acid melt curve. The procedure is repeated with additional target nucleic acid template(s) to generate additional melt curve(s). The additional melt curve(s) are compared with the standard curve to yield minor differences that may be indicative of different genes or mutation site(s) in the target nucleic acid template sequences (U.S. Pat. Nos. 7,387, 887; 7,456,281; and 7,582,429).

In some embodiments, a method of the invention is used to perform multiplexed high resolution melt curve analysis to monitor signal amplification from more than one target nucleic acid template sequences with multiple ICR probes in the same reaction.

In certain aspects, the invention provides for systems that can be used to detect target analytes, such as nucleic acids. The system can include at least one detector (e.g., a spectrometer, etc.) that detects a signal that is indicative of a target analyte. For example, the system can include a detector for measuring an optical signal, such as fluorescence. In addition, the system can include at least one thermal modulator (e.g., a thermal cycling device, etc.) operably connected to a container or solid support to modulate temperature of a sample. The thermal modulator can be used for performing isothermal signal amplification, nucleic acid amplification methods, melting curve analysis, and/or hybridization assays.

In some embodiments, detectors can be structured to detect detectable signals produced, e.g., in or proximal to another component of the given assay system (e.g., in container, on a solid support, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond to real-time events. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5$^{th}$ Ed., Harcourt Brace College Publishers (998) and Currell, *Analytical Instrumentation: Performance Characteristics and Quality*, John Wiley & Sons, Inc. (2000), both of which are incorporated by reference.

In some embodiments, the systems of the invention can include controllers that are operably connected to one or more components (e.g., detectors, thermal modulators, fluid transfer components, etc.) of the system to control operation of the components. More specifically, controllers can be included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which can function to instruct the operation of these instruments in accordance with preprogrammed or user input instructions, receive data and information from these instruments, and interpret, manipulate and report this information to the user.

Controllers are Available from Various Commercial Sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

In some embodiments, the computer can include appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

In some embodiments, the invention provides integrated systems for performing ICR and for making $T_m$ determinations. The systems can include instrumentation and tools for interpreting and analyzing collected data, especially including tools for determining quantity of amplified linkage products and for deriving $T_m$. These tools can include algorithms and/or the ability to electronically store information (e.g., collected fluorescence data, predetermined $T_m$ correlations, etc.). Each part of an integrated system can be functionally interconnected, and in some cases, physically connected. In some embodiments, the integrated system is automated, where there is no requirement for any manipulation of the sample or instrumentation by an operator following initiation of the ICR or $T_m$ analysis.

In some embodiments, a system of the invention can include instrumentation. For example, the invention can include a detector such as a fluorescence detector (e.g., a fluorescence spectrophotometer). A detector or detectors can be used in conjunction with the invention, e.g., to monitor/measure the emission from a light emitting moiety, such as a nucleic acid dye. A detector can be in the form of a multi-well plate reader to facilitate the high-throughput capacity of the assays described herein.

In some embodiments, the integrated system includes a thermal cycling device, or thermocycler, for the purpose of controlling the temperature of the $T_m$ melting analysis or for modulating the temperature for performing linkage product amplification. In some embodiments, the thermal cycling device and the detector are an integrated instrument, where the thermal cycling and emission detection (e.g., fluorescence detection) are performed in the same device.

In some embodiments, a detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the $T_m$ of the target hybridization complex and/or the concentration of amplified or target nucleic acid is determined. In some embodiments, the correlation module comprises a computer program that calculates the $T_m$ or the concentration of nucleic acid based on the fluorescence readings from the detector, and in some cases, optionally derives sequence and/or genotype information of an unknown sample based on the $T_m$ and/or ICR result. In some embodiments, the correlation module compares the $T_m$ of the unknown sample with a database (or table) of $T_m$ values for known sequences and/or genotypes to make a correlation between the $T_m$ of the unknown sample and the sequence or genotype of the known sample.

In some aspects, a system of the invention for the determination of a $T_m$ of a hybridization complex and/or for performing ICR comprises a reagent composition, a thermal control device for regulating the temperature reaction over a range of temperatures, and a detector for measuring the signal from the melting reaction over the range of temperatures. In some cases, the system also includes a correlation module that is operably coupled to the detector and receives signal measurements, where the correlation module correlates the signal intensity with the concentration of the target analyte or the melting temperature of the target analyte.

The following examples are intended to further illustrate certain embodiments of the invention and are not to be construed to limit the scope of the invention.

Example 1

ICR Amplification Method

The strategy and expected results from an exemplary Isothermal Chain Reaction ("ICR"), in which bond-forming reactive moieties (BFRMs) join the 5' and 3' termini of a probe nucleic acid (probe) annealed to a nucleic acid template and lower the probe $T_m$ to enable the amplification of autoligated probe linkage products at a constant temperature through a continuous isothermal progression of hybridization and denaturation of the probe from a target nucleic acid template sequence, such as a DNA biomarker, are shown (FIG. 1). Isothermal amplification with ICR, in which a probe containing a self-complementary region (SR) forms a stem structure and a target-complementary region (TR) loop structure in the absence of target nucleic acid template. The 5' and 3' termini of the probe contain a first bond-forming reactive moiety (BFRM1) that is inactive in the stem conformation (FIG. 1A). In the presence of a target nucleic acid template sequence, the TR hybridizes to the template and separates the SR, placing BFRM1 in an active conformation (FIG. 1B). A universal linker (UL) containing a second bond-forming reactive moiety (BFRM2) at the 5' and 3' termini autoligates to the probe through the BFRM1 and constricts the TR sequences annealed to the target nucleic acid template, lowering the $T_m$ of the probe (FIG. 1C). The constricted autoligated ICR probe product releases from the template without thermocycling, and a new probe follows and re-interrogates the native target sequence, continuing the cycle of template-mediated isothermal probe linkage product amplification without any enzymes, nucleotides, primers, or extension reactions (FIG. 1D). Because the probe autoligated to the UL has a lower $T_m$ than the isothermal temperature of the reaction, the autoligation complex rapidly melts off the template and provides an entry point for a new probe, which has a higher $T_m$ to quickly hybridize to the template. ICR probes selectively interrogate native target SNPs without hybridizing to non-target template sequences. A variety of bond-forming reactive moieties can be used with the methods described herein, which are not limited to any specific bond-forming chemistry.

Example 2

ICR with FRET Detection

Figure 2:
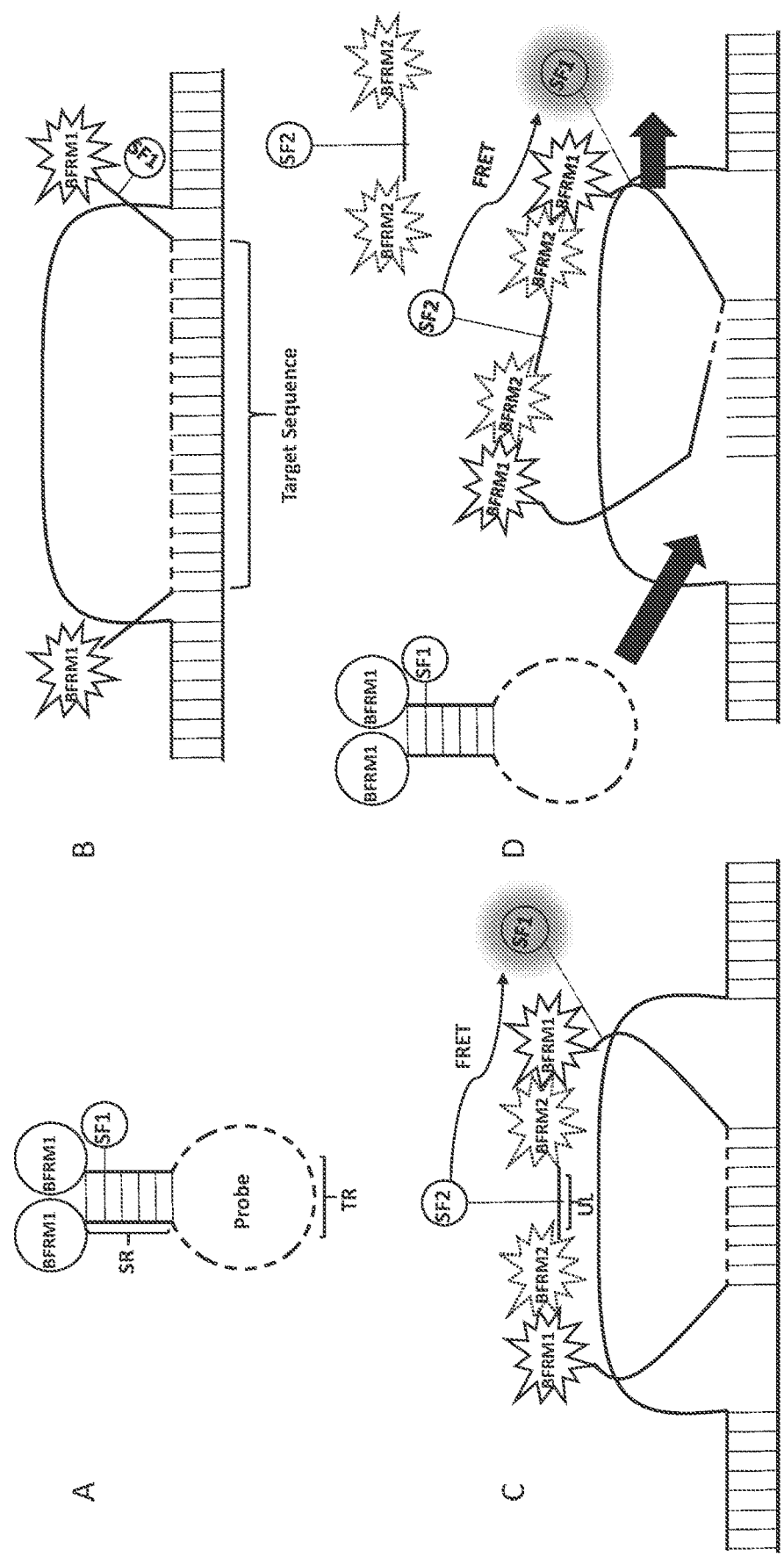
FIG. 2 illustrates an exemplary strategy and expected results from isothermal amplification with ICR and detection by FRET between a donor and acceptor signal fluorophore. Various fluorophores and detection groups can be used with ICR.

The strategy and expected results from an exemplary ICR for detection with a first signal fluorophore (SF1) and a second signal fluorophore (SF2) by FRET, in which BFRMs join the 5' and 3' termini of a probe annealed to nucleic acid template to bring SF1 and SF2 in close proximity for FRET detection at a constant temperature through a continuous isothermal progression of hybridization and denaturation of the probe from a target nucleic acid template sequence, such as a DNA biomarker, are shown (FIG. 2). Isothermal amplification with ICR, in which the probe contains SF1 that is incorporated near the 3' terminus (FIG. 2A). In the presence of a target nucleic acid template sequence, the TR hybridizes to the template and separates the SR, placing BFRM1 in an active conformation (FIG. 2B). A UL contains SF2 and BFRM2 at the 5' and 3' termini, and autoligates to the probe through the BFRM1 and places SF1 and SF2 in close proximity, resulting in a FRET reaction (FIG. 2C). The constricted autoligated ICR probe linkage product releases from the template and initiates a signal amplification chain reaction without thermocycling, where a new probe follows and re-interrogates the native target sequence, continuing the cycle of template-mediated isothermal signal amplification without any enzymes, nucleotides, primers, or extension reactions (FIG. 2D). Various fluorophores and detection groups can be used with the methods described herein, which are not limited to any specific detection chemistry.

Example 3

ICR with Quencher/Fluorophore Detection

Figure 3:
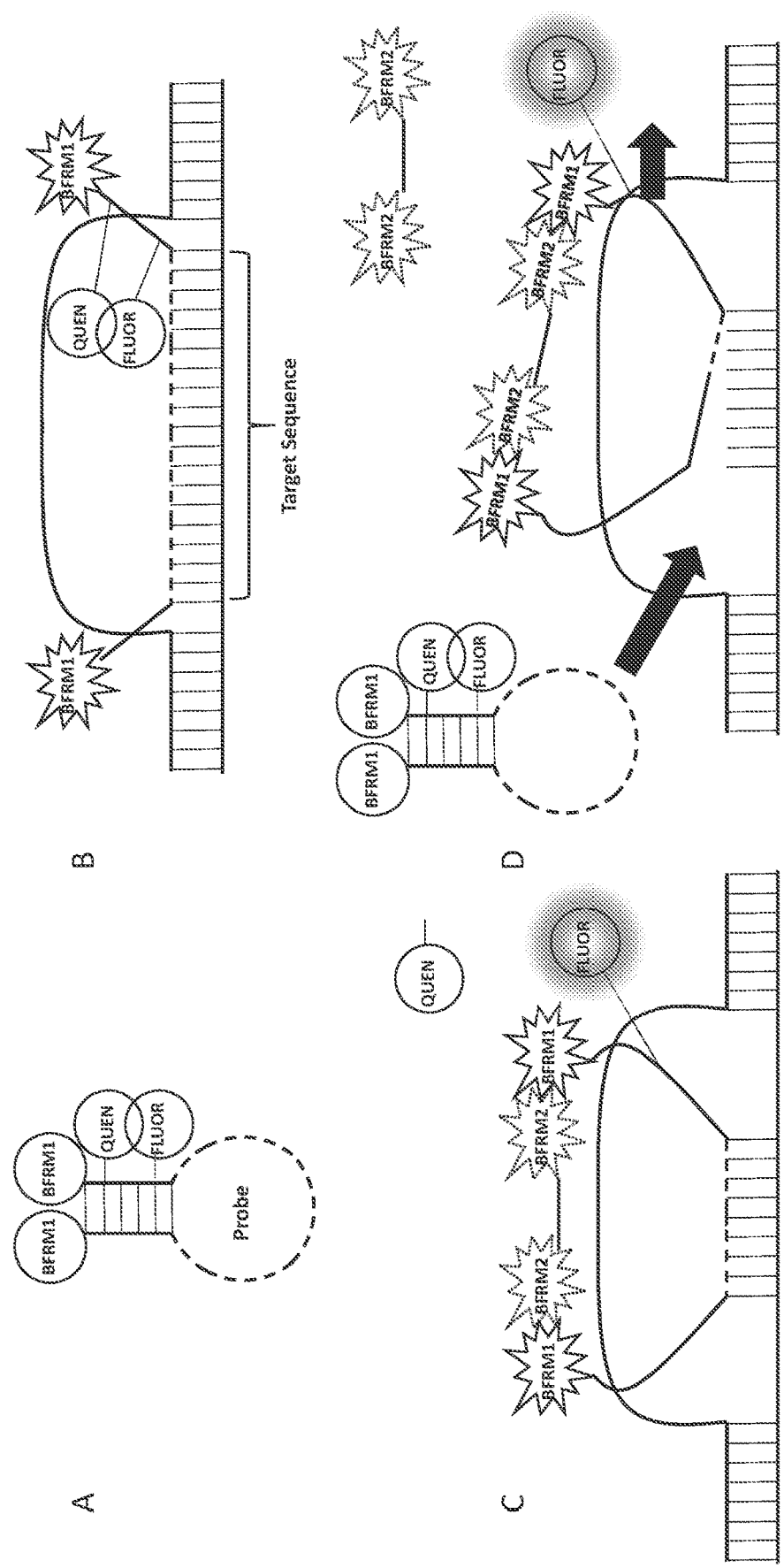
FIG. 3 illustrates an exemplary strategy and expected results from isothermal amplification with ICR and detection by a removal of a quenching moiety from a detectable group. Various detection methods can be used with ICR.

The strategy and expected results from an exemplary ICR for detection with release of a quenching moiety (QUEN) from a fluorophore (FLUOR), in which linkage between the probe and UL separates the QUEN from the FLUOR before the probe linkage product is detected at a constant temperature through a continuous isothermal progression of hybridization and denaturation of the probe from a target nucleic acid template sequence, such as a DNA biomarker, are shown (FIG. 3). Isothermal amplification with ICR, in which the probe contains QUEN and FLUOR near the 3' terminus (FIG. 3A). In the presence of a target nucleic acid template sequence, the TR hybridizes to the template and separates the SR, placing BFRM1 in an active conformation (FIG. 3B). A UL contains BFRM2 at the 5' and 3' termini, and autoligates to the probe through the BFRM1 to release the QUEN, resulting in signal fluorescence from FLUOR (FIG. 3C). The constricted autoligated ICR probe linkage product releases from the template and initiates a signal amplification chain reaction without thermocycling, where a new probe follows and re-interrogates the native target sequence, continuing the cycle of template-mediated isothermal signal amplification without any enzymes, nucleotides, primers, or extension reactions (FIG. 3D). Various fluorophores and detection groups can be used with the methods described herein, which are not limited to any specific detection chemistry. A variety of detection methods can be used with the methods described herein, which are not limited to any specific detection method.

Example 4

ICR with Nucleic Acid Binding Dye Detection

Figure 4:
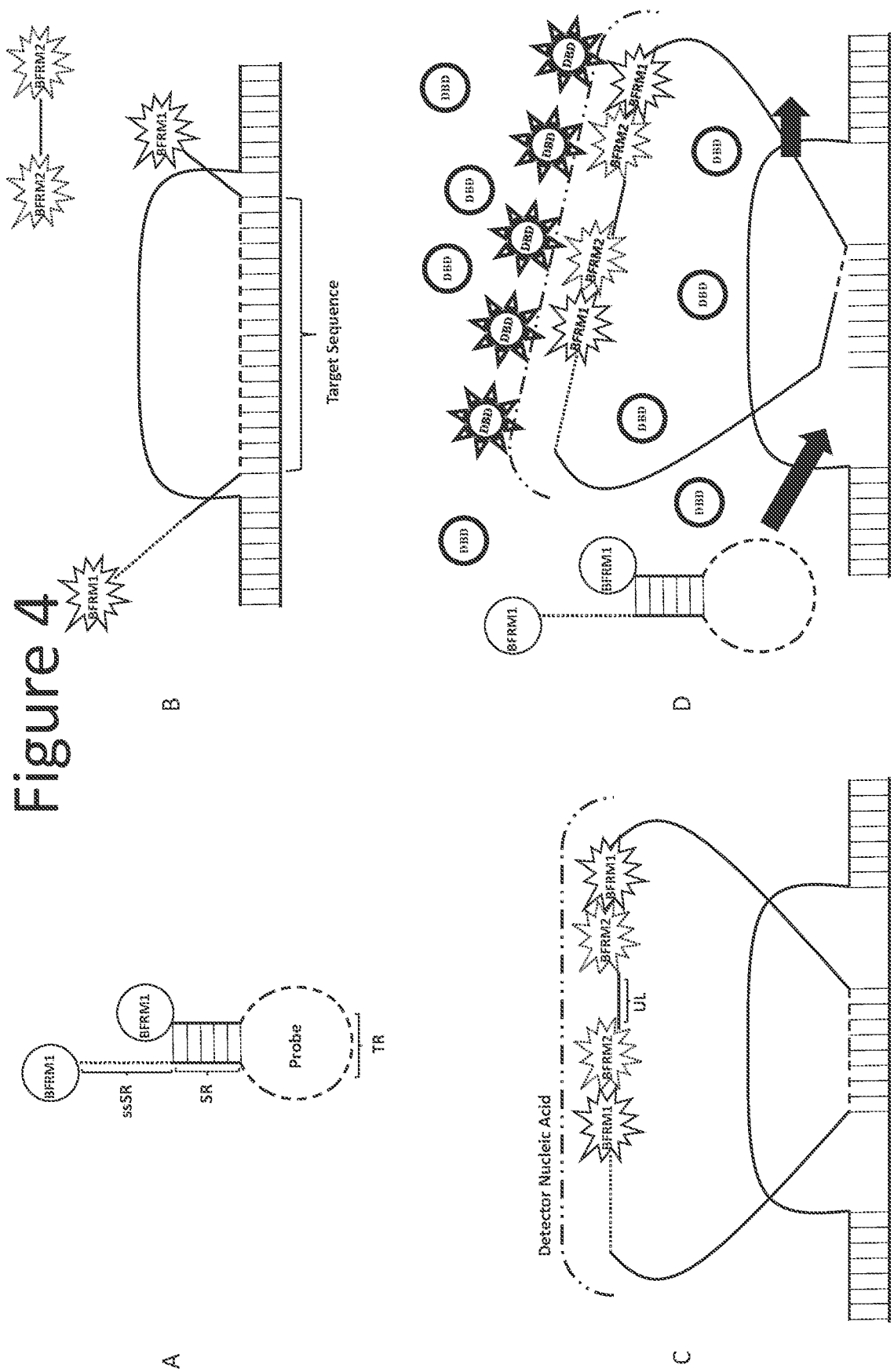
FIG. 4 illustrates an exemplary strategy and expected results from isothermal amplification with ICR and detection with a double-stranded nucleic acid binding dye and a detector nucleic acid. Various lengths of detector nucleic acids can be used with ICR.

The strategy and expected results from an exemplary ICR for detection with a double-stranded nucleic acid binding dye (DBD), in which DBD binds to a double-stranded region formed by the hybridization of a detector nucleic acid to sequences that flank BFRM1-BFRM2 junction sites in a probe linkage product, including ssSR, SR, and UL sequences, are shown (FIG. 4). The probe contains a 5' single-stranded SR region (ssSR), wherein the bases are unpaired and the BFRM1 is overhanging at the 5' terminus and the BFRM1 is recessed at the 3' terminus (FIG. 4A). In the presence of a target nucleic acid template sequence, the TR hybridizes to the template and separates the SR, placing BFRM1 in an active conformation with the ssSR extended from the 5' terminus in the probe (FIG. 4B). A UL contains BFRM2 at the 5' and 3' termini and autoligates to the probe through the BFRM1 to generate a template for the detector nucleic acid to hybridize to, wherein the detector nucleic acid annealed to the joined SR/ssSR/UL sequences forms a double-stranded region (FIG. 4C). The constricted autoligated ICR probe linkage product releases from the template and DBDs bind to the double-stranded region to initiate a signal amplification chain reaction without thermocycling, where a new probe follows and re-interrogates the native target sequence, continuing the cycle of template-mediated isothermal signal amplification without any enzymes, nucleotides, primers, or extension reactions (FIG. 4D). Various fluorophores and detection groups can be used with the methods described herein, which are not limited to any specific detection chemistry. A variety of detection methods can be used with the methods described herein, which are not limited to any specific detection method. A "detector nucleic acid" refers to polynucleotides derived from mononucleotides, such as DNA and RNA, which contains a single-stranded nucleotide sequence that hybridizes to nucleotides in the ssSR, SR, and UL, wherein the detector nucleic acid is annealed. Various lengths of ssSR regions and detector nucleic acids can be used for single channel multiplexing with ICR.

Example 5

ICR Single-Channel Multiplexing Method

Figure 5:
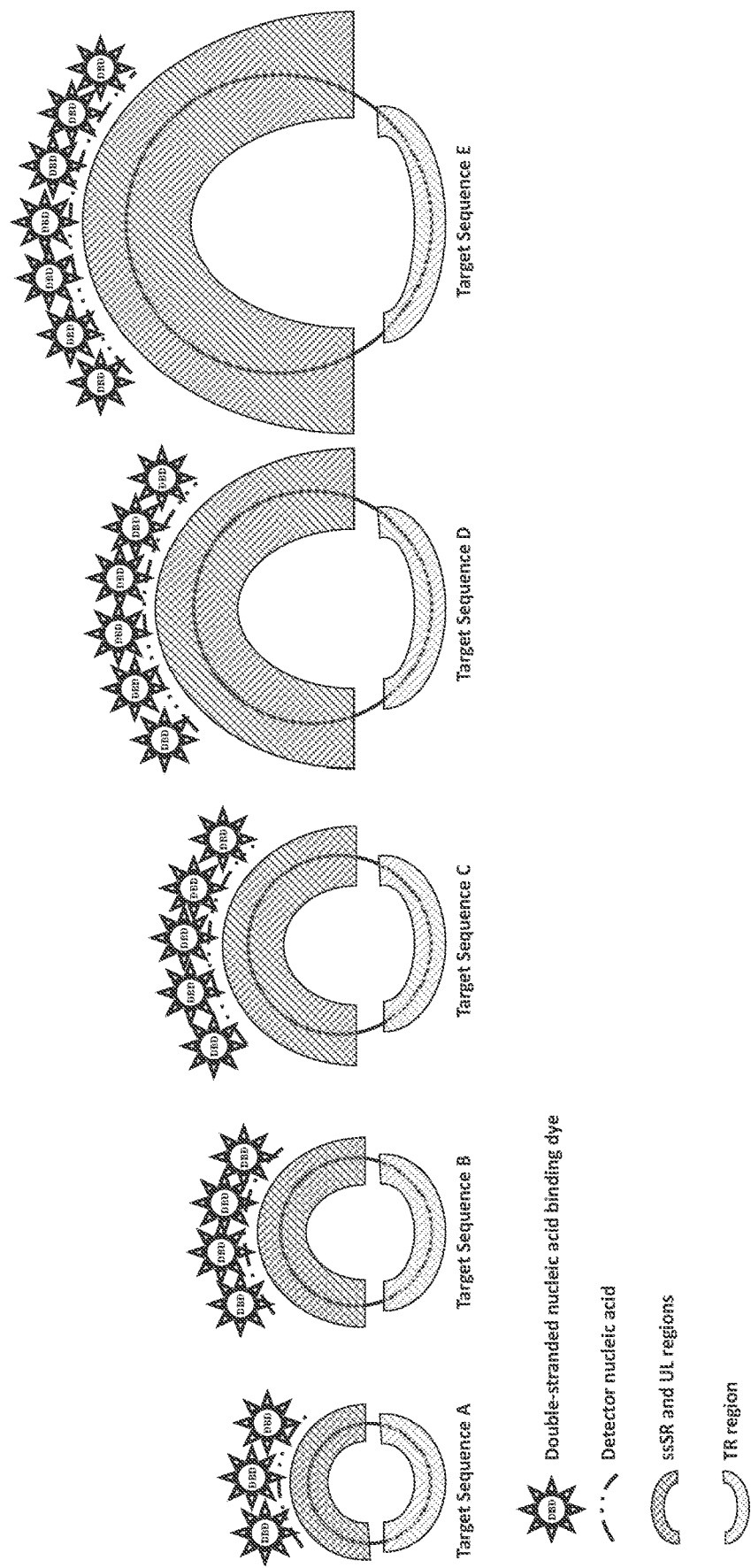
FIG. 5 shows that increasing the single-stranded SR region (ssSR) and detector nucleic acid lengths increases the $T_m$ of the duplex. This illustrates that various lengths of ssSRs and detector nucleic acids can be used for single channel multiplexing with ICR.

The strategy for an exemplary ICR single-channel multiplexing with a double-stranded nucleic acid binding dye (DBD) is shown (FIG. 5). ICR probes to five different target nucleic acid template sequences (A-E) contain ssSRs and detector nucleic acids that increase in length, which form double-stranded regions with increasing $T_m$s in the probe linkage products. In the presence of a DBD, a specific $T_m$ for each probe linkage product is associated with the respective target sequence to enable multiplexing with a single dye or detectable group.

Example 6

ICR Detection with FRET in Real-Time

Figure 6:
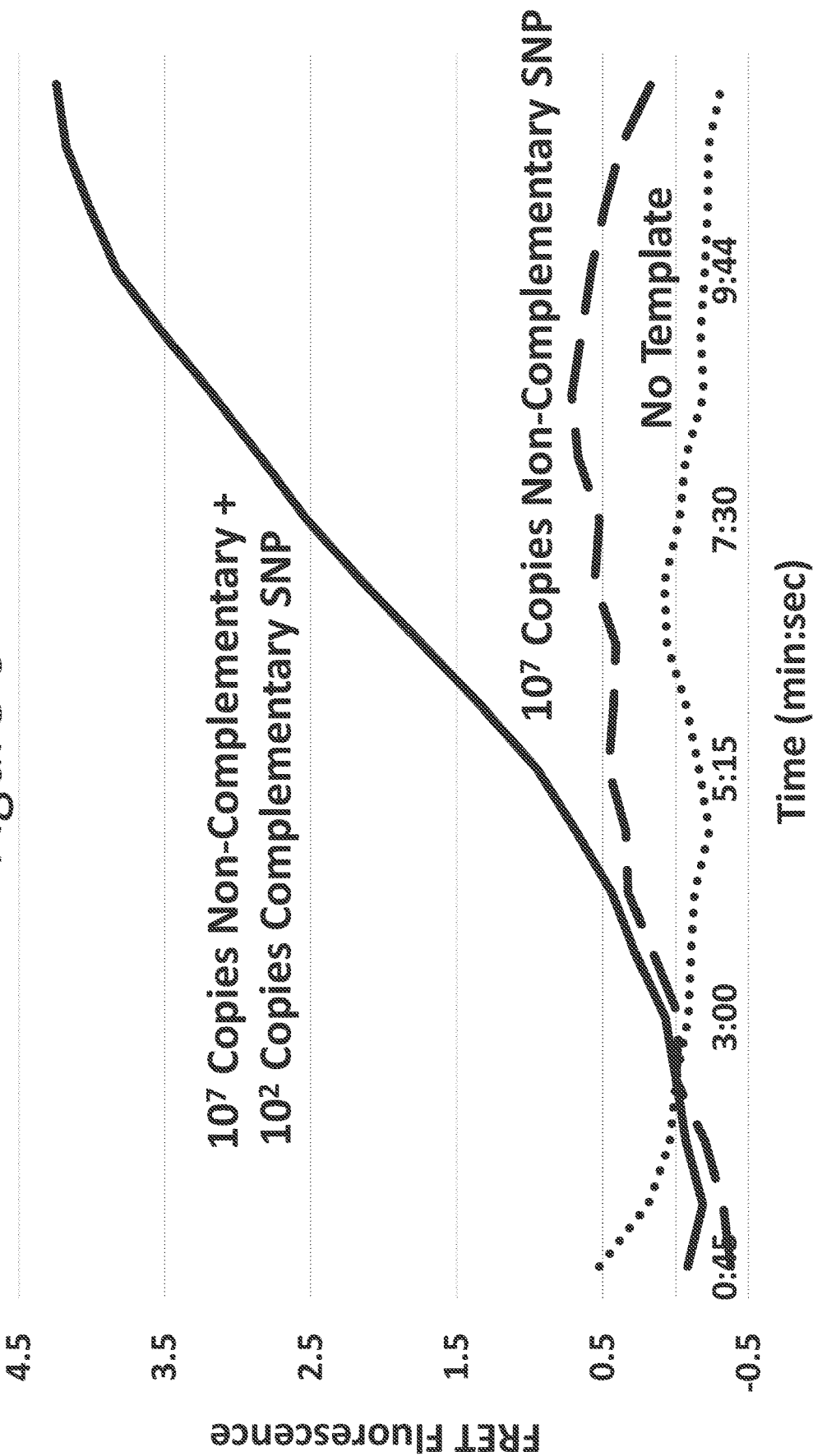
FIG. 6 shows real-time amplification plots using FRET fluorescence to demonstrate ICR isothermal amplification and detection of $10^2$ copies of a complementary SNP in the presence of $10^5$ copies of a non-complementary SNP in under 5 minutes. This demonstrates the speed, selectivity, and specificity of ICR for a SNP variant in a heterogeneous mixture of nucleic acid template.

The results of an exemplary ICR self-ligation reactions using Fluorescein/TAMRA FRET fluorescence detection to demonstrate isothermal amplification with an ICR probe in the presence or absence of a complementary SNP template are shown (FIG. 6). The reactions were carried out isothermally at 60° C. and autoligation products were monitored by real-time FRET fluorescence. The real-time amplification plots show signal amplification in under 5 minutes for a reaction with $10^2$ copies of double-stranded oligo template containing a complementary SNP template mixed with $10^7$ copies of double-stranded oligo containing a non-complementary SNP (solid line). No amplification signal is observed in the reaction with $10^7$ copies of the non-complementary SNP alone (dashed line) or the reaction without a template (dotted line). This illustrates that ICR has the speed, selectivity, and specificity to detect a rare SNP variant in less than 5 minutes without thermocycling in real-time, and therefore ICR can be used for rare mutation detection in heterogeneous samples and point-of-care testing.

Reactions were performed according to the strategy shown in FIG. 2. The ICR probe contains a hydroxyl group (BFRM1) at the 5' and 3'-termini, while the UL contains a 1-ethyl-3-(3-dimethylaminopropyl) carbodiimide (EDC)-activated phosphate group modification (BFRM2) at the 5 and 3' termini. FRET between a TAMRA modification of a T base in the probe (SF1) and a Fluorescein modification of a T base in the UL (SF2) was used to monitor signal amplification. Double-stranded oligonucleotides were used as templates containing a either a SNP complementary to the probe or a non-complementary SNP. Reactions were run isothermally at 60° C. on a real-time thermocycler instrument. The baselined data were exported into Excel, and the plots were smoothed by a 4-point rolling average of the data.

Example 7

ICR Detection with SYBR Green in Real-Time

Figure 7:
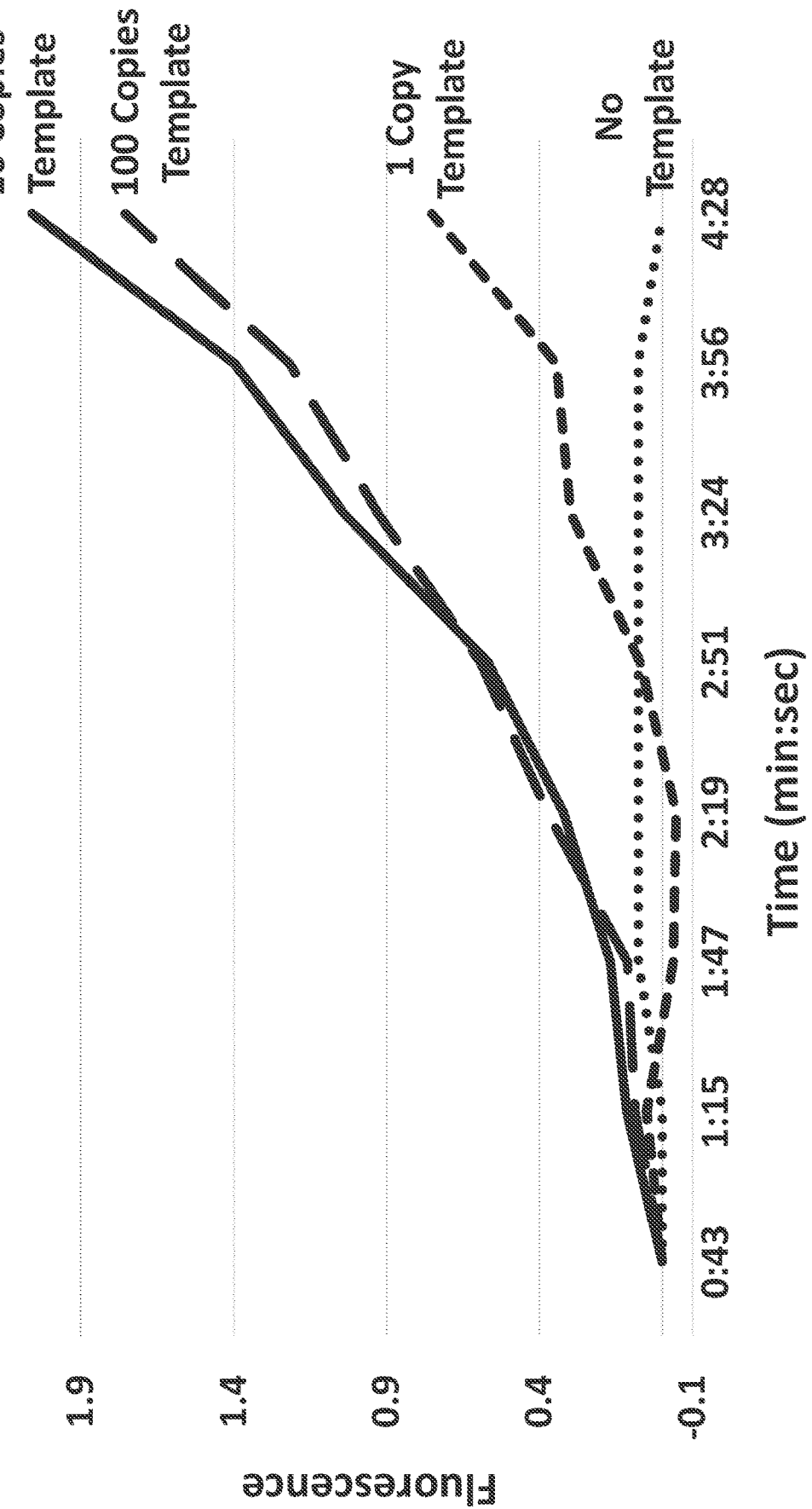
FIG. 7 shows real-time amplification plots using a detector nucleic acid and fluorescence from a double-stranded nucleic acid binding dye to demonstrate ICR isothermal amplification and detection of a theoretical 1 copy of SNP in under 5 minutes. This demonstrates the speed and sensitivity of ICR for a target nucleic acid template.

The results of an exemplary ICR self-ligation reactions using SYBR Green fluorescence detection to demonstrate isothermal amplification with an ICR probe in the presence of increasing copy numbers of a complementary template are shown (FIG. 7). The reactions were carried out isothermally at 60° C. and autoligation products were monitored by real-time SYBR Green fluorescence. The real-time amplification plots show signal amplification in under 5 minutes for reactions containing $10^2$ (long-dashed line), $10^1$ (solid line), and a theoretical single copy number (short-dashed line) of double-stranded oligo complementary template. No amplification signal is observed in the reaction without a template (dotted line). This illustrates that ICR has the speed and sensitivity to detect a template with a theoretical copy number of 1 in less than 5 minutes without thermocycling in real-time, and therefore ICR can be used for rare mutation detection in limiting heterogeneous samples and point-of-care testing.

Reactions were performed according to the strategy shown in FIG. 4. The ICR probe contains a hydroxyl group (BFRM1) at the 5' and 3'-termini, while the UL contains a 1-ethyl-3-(3-dimethylaminopropyl) carbodiimide (EDC)-activated phosphate group modification (BFRM2) at the 5 and 3' termini. A detector nucleic acid was included in each reaction and SYBR fluorescence was used to monitor signal amplification. Signal amplifications from 4 replicates were averaged for each copy number designation. Double-stranded oligonucleotides were used as templates. Reactions were run isothermally at 60° C. on a real-time thermocycler instrument. The baselined data were exported into Excel, and the plots were smoothed by a 5-point rolling average of the data.

Example 8

ICR Thermocycled Detection with FRET in Crude Samples in Real-Time

Figure 8:
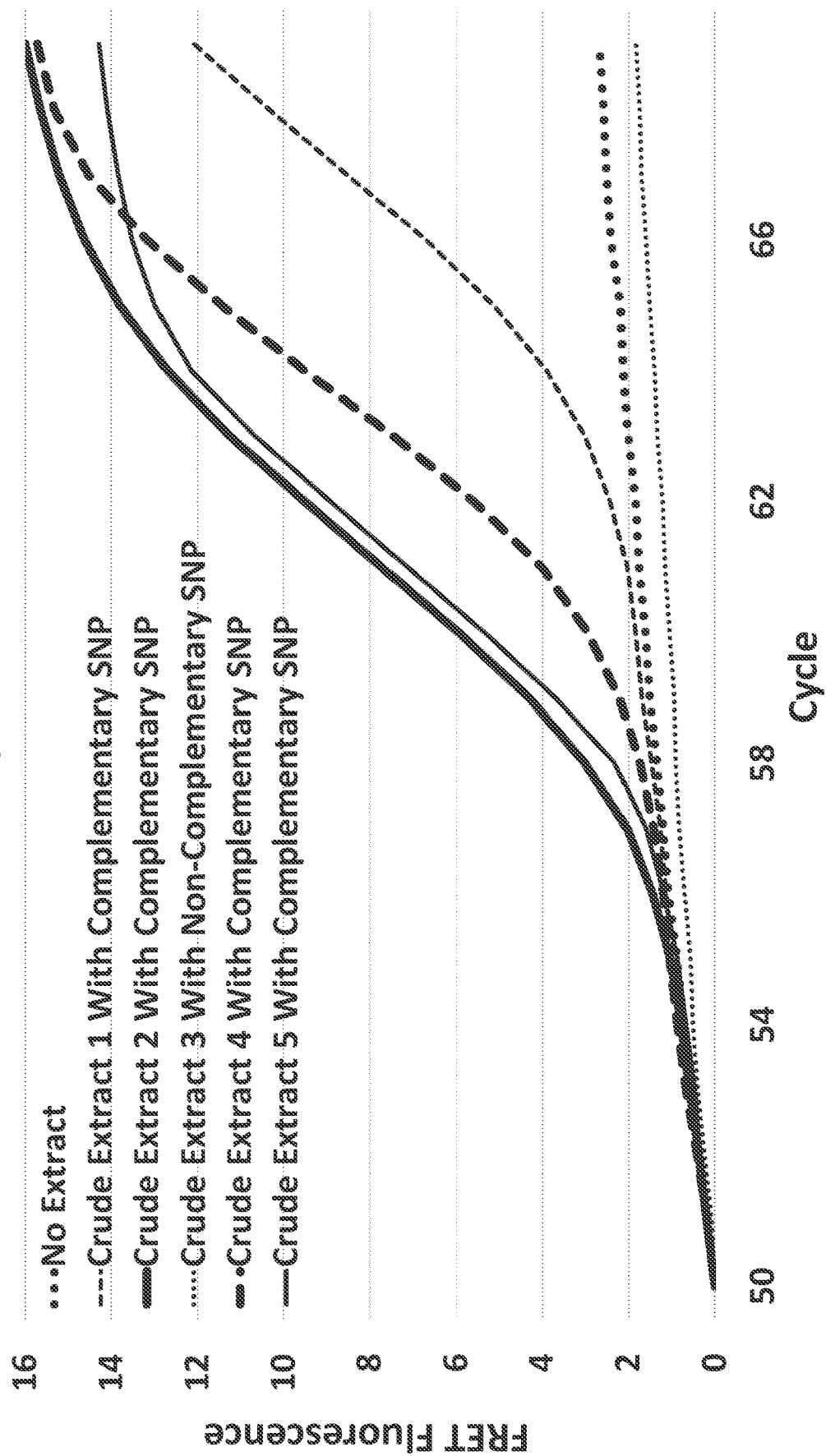
FIG. 8 shows real-time amplification plots of FRET fluorescence to demonstrate ICR thermocycled amplification and detection of a complementary SNP in genomic DNA from crude extracts that inhibit PCR. This demonstrates resistance of ICR to enzyme inhibitors.

The results of an exemplary ICR self-ligation reactions using Fluorescein/TAMRA FRET fluorescence detection to demonstrate amplification by thermocycling with an ICR probe in the presence of a genomic nucleic acid template containing either a complementary or non-complementary SNP isolated from 5 crude extracts that inhibit PCR are shown (FIG. 8). The reactions were thermocycled and the autoligation probe linkage products were monitored by real-time FRET fluorescence. The real-time amplification plots show signal amplification of genomic DNA in crude extracts that contain the complementary SNP (extracts 1-dashed line, 2-thick solid line, 4-thick dashed line, and 5-solid line) but not in the crude extract that contains the non-complementary SNP (extract 3-dotted line) or the no-extract control (thick dotted line). All extracts were previously shown to inhibit PCR, and SNPs were confirmed by sequencing purified samples (data not shown). The high cycle numbers to generate a signal are due to low copy numbers of SNP templates (estimated at <5 copies of SNP for all reactions), and slower chemistry reaction kinetics of the BFRM1 and BFRM2 used in the reactions. Cycles 50-74 are shown for illustration. These results show ICR is able to identify SNP variants in samples containing polymerase inhibitors, and illustrate that ICR has the sample tolerance and sensitivity to detect a SNP variant in unpurified extracts in real-time, and therefore ICR can be used for rare mutation detection in samples and specimens that contain enzyme inhibitors and for point-of-care testing.

Reactions were performed according to the strategy shown in FIG. 2. The ICR probe contains a cyclooctyne modification (BFRM1) at the 5' and 3'-termini, while the UL contains an azide modification (BFRM2) at the 5' and 3' termini. FRET between a TAMRA modification of a T base in the probe (SF 1) and a Fluorescein modification of a T base in the UL (SF2) was used to monitor signal amplification. Genomic DNA containing either a complementary SNP or non-complementary SNP isolated from crude extracts was used as template. Reactions were thermocycled for 74 cycles at 95° C. for 45 seconds and 37° C. for 1 minute on a real-time thermocycler instrument. The baselined data were exported into Excel, and the plots were smoothed by a 6-point rolling average of the data.

What is claimed is:

1. A method of detecting and identifying a pathogen that comprises a nucleic acid molecule comprising a target nucleic acid template sequence in a sample, the method comprising:
    (a) forming a reaction solution comprising a nucleic acid molecule comprising a target nucleic acid template sequence, a probe nucleic acid ("probe"), and a universal linker ("UL"), wherein the probe comprises two or more first reactive moieties, and the universal linker comprises two or more second reactive moieties, each first reactive moiety being capable of reacting with a second reactive moiety to form a bond, wherein the probe comprises a nucleic acid sequence comprising, in 5' to 3' order:
        (i) a first self-complementary region ("SR1");
        (ii) a target-complementary region ("TR") comprising a nucleic acid sequence complementary to the target nucleic acid template sequence; and
        (iii) a second self-complementary region ("SR2") comprising a nucleic acid sequence complementary to the first self-complementary region;
    wherein, in the absence of the target nucleic acid template sequence, the first self-complementary region hybridizes with the second self-complementary region such that the probe acquires a stem-loop structure and wherein bond formation between the first reactive moieties and the second reactive moieties is inhibited by the stem-loop structure; and
    (b) incubating the reaction solution at an incubation temperature such that:
        (1) the target-complementary region of the probe hybridizes to the target nucleic acid template sequence with a first melting temperature that is higher than the incubation temperature, wherein hybridization of the target-complementary region to the target nucleic acid template sequence disrupts the stem-loop structure of the probe, thereby disinhibiting reaction of the first reactive moieties with the second reactive moieties; and
        (2) the first reactive moieties of the hybridized probe form chemical bonds with the second reactive moieties of the linker to form a linkage product, wherein the linkage product has a melting temperature for the target nucleic acid template sequence that is lower than the incubation temperature such that the linkage product disassociates from the target nucleic acid template sequence at the incubation temperature; and
    (c) detecting the linkage product by detecting change in a signal emitted by a detectable moiety, wherein detecting the linkage product is an indication of detecting the nucleic acid molecule comprising a target nucleic acid template sequence, thereby detecting and identifying the pathogen.

2. The method of claim 1, wherein step (c) comprises detecting a fluorescence signal by FRET.

3. The method of claim 1, wherein step (c) comprises detecting loss of a signal emitted by the detectable moiety.

4. The method of claim 1, wherein step (c) comprises detecting a signal emitted by the detectable moiety.

5. The method of claim 1, wherein the formation of the linkage product results in the separation of the detectable moiety from a quenching moiety and step (c) comprises detecting a signal emitted by the detectable moiety.

6. The method of claim 1, wherein step (c) comprises detecting the linkage product using a double-stranded nucleic acid binding dye.

7. The method of claim 1, wherein the sample is a biological sample.

8. The method of claim 7, wherein the biological sample is blood, urine, spinal fluid, cerebrospinal fluid, synovial fluid, amniotic fluid, semen, or saliva.

9. A method of detecting and identifying a pathogen that comprises a nucleic acid molecule, the nucleic acid molecule comprising a target nucleic acid template sequence, the method comprising:
  (a) forming a reaction solution comprising a nucleic acid molecule comprising a target nucleic acid template sequence, a probe nucleic acid ("probe"), a universal linker ("UL"), and a detector nucleic acid ("detector"), wherein the probe comprises two or more first reactive moieties, and the universal linker comprises two or more second reactive moieties, each first reactive moiety being capable of reacting with a second reactive moiety to form a bond, wherein the probe comprises a nucleic acid sequence comprising, in 5' to 3' order:
    (i) a single-stranded region ("ssSR");
    (ii) a first self-complementary region ("SR1");
    (iii) a target-complementary region ("TR") comprising a nucleic acid sequence complementary to the target nucleic acid template sequence; and
    (iv) a second self-complementary region ("SR2") comprising a nucleic acid sequence complementary to the first self-complementary region;
    wherein, in the absence of a target nucleic acid template sequence, the first self-complementary region in the probe hybridizes with the second self-complementary region such that the probe acquires a stem-loop structure and wherein bond formation between the first reactive moiety and the second reactive moiety is inhibited by the stem-loop structure; and
  (b) incubating the reaction solution at an incubation temperature such that:
    (1) the target-complementary region of a probe hybridizes to a target nucleic acid template sequence with a first melting temperature that is higher than the incubation temperature, wherein hybridization of the target-complementary region from a probe to the target nucleic acid template sequence disrupts the stem-loop structure of the probe, thereby disinhibiting reaction of the first reactive moiety with the second reactive moiety; and
    (2) the first reactive moiety of the hybridized probe forms a chemical bond with the second reactive moiety of the linker to form a linkage product in the same reaction, wherein the linkage product has a melting temperature corresponding to its target nucleic acid template sequence, which is lower than the incubation temperature such that the linkage product disassociates from its corresponding target nucleic acid template sequence at the incubation temperature; and
  (c) detecting the linkage product by a double-stranded nucleic acid binding dye, wherein a detector nucleic acid hybridizes to a nucleotide in the ssSR, SR1, SR2, or UL in the linkage product to form a double-stranded nucleic acid region for a nucleic acid binding dye to intercalate and bind, wherein detecting the linkage product is an indication of detecting the nucleic acid molecule comprising a target nucleic acid template sequence, thereby detecting and identifying the pathogen.

10. The method of claim 9, wherein the probe nucleic acid, universal linker, detector nucleic acid, and/or probe linkage product are immobilized onto a solid support substrate.

11. The method of claim 9, wherein the probe nucleic acid, universal linker, detector nucleic acid, and/or probe linkage product are arrayed onto a solid support substrate.

* * * * *